(12) United States Patent
Alli et al.

(10) Patent No.: US 12,071,497 B2
(45) Date of Patent: *Aug. 27, 2024

(54) HIGH REFRACTIVE INDEX, HIGH ABBE COMPOSITIONS

(71) Applicant: JOHNSON & JOHNSON SURGICAL VISION, INC., Irvine, CA (US)

(72) Inventors: Azaam Alli, Jacksonville, FL (US); Bart A. Johnson, Laguna Beach, CA (US); Scott L. Joslin, Ponte Vedra Beach, FL (US)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/309,715

(22) Filed: Apr. 28, 2023

(65) Prior Publication Data
US 2023/0279169 A1    Sep. 7, 2023

Related U.S. Application Data

(63) Continuation of application No. 16/861,032, filed on Apr. 28, 2020, now Pat. No. 11,708,440.

(60) Provisional application No. 62/842,993, filed on May 3, 2019.

(51) Int. Cl.
| | |
|---|---|
| *C08F 220/18* | (2006.01) |
| *A61F 2/16* | (2006.01) |
| *C08F 220/28* | (2006.01) |
| *C08K 5/5397* | (2006.01) |
| *C08L 33/26* | (2006.01) |
| *C08L 39/06* | (2006.01) |
| *C08L 83/06* | (2006.01) |
| *G02B 1/00* | (2006.01) |
| *G02B 1/04* | (2006.01) |
| *G02C 7/02* | (2006.01) |

(52) U.S. Cl.
CPC .......... *C08F 220/1806* (2020.02); *A61F 2/16* (2013.01); *C08F 220/281* (2020.02); *C08K 5/5397* (2013.01); *C08L 33/26* (2013.01); *C08L 39/06* (2013.01); *C08L 83/06* (2013.01); *C08L 2201/10* (2013.01); *C08L 2312/00* (2013.01); *G02B 1/007* (2013.01); *G02B 1/043* (2013.01); *G02C 7/022* (2013.01)

(58) Field of Classification Search
CPC ................................................. G02B 1/043
See application file for complete search history.

(56) References Cited

U.S. PATENT DOCUMENTS

| | | |
|---|---|---|
| 4,131,729 A | 12/1978 | Schmitt et al. |
| 4,573,998 A | 3/1986 | Mazzocco |
| 4,731,079 A | 3/1988 | Stoy |
| 5,233,007 A | 8/1993 | Yang |
| 5,290,892 A | 3/1994 | Namdaran et al. |
| 5,357,024 A | 10/1994 | Leclaire |
| 5,403,901 A | 4/1995 | Namdaran et al. |
| 5,424,339 A | 6/1995 | Zanka et al. |
| 5,433,746 A | 7/1995 | Namdaran et al. |
| 5,541,278 A | 7/1996 | Raleigh et al. |
| 5,648,402 A | 7/1997 | Nunez et al. |
| 5,674,960 A | 10/1997 | Namdaran et al. |
| 5,693,095 A | 12/1997 | Freeman et al. |
| 5,694,195 A | 12/1997 | Engardio et al. |
| 5,861,031 A | 1/1999 | Namdaran et al. |
| 5,910,537 A | 6/1999 | Feingold et al. |
| 5,913,898 A | 6/1999 | Feingold |
| 6,140,438 A | 10/2000 | Ojio et al. |
| 6,313,187 B2 | 11/2001 | LeBoeuf et al. |
| 6,313,251 B1 | 11/2001 | Toh et al. |
| 6,353,069 B1 | 3/2002 | Freeman et al. |
| 6,367,929 B1 | 4/2002 | Maiden et al. |
| 6,416,550 B2 | 7/2002 | Freeman |
| 6,491,721 B2 | 12/2002 | Freeman et al. |
| 6,699,953 B2 | 3/2004 | Oshikiri et al. |
| 6,770,735 B2 | 8/2004 | Tanaka et al. |
| 6,852,793 B2 | 2/2005 | Salamone et al. |
| 7,009,024 B2 | 3/2006 | Salamone et al. |

(Continued)

FOREIGN PATENT DOCUMENTS

| | | |
|---|---|---|
| AU | 734097 B2 | 6/2001 |
| CA | 2059328 A1 | 10/1992 |

(Continued)

OTHER PUBLICATIONS

Son H.S., et al., "In Vitro Optical Quality Measurements of Three Intraocular Lens Models Having Identical Platform," BMC Ophthalmology, Jun. 2017, vol. 17(1), 9 pages, XP093025659, Retrieved from the Internet:[URL: http://link.springer.com/content/pdf/10.1186/s12886-017-0460-0.pdf].

Windbiel, J.T., et al., "Microgel Preparation by Miniemulsion Polymerization of Passerini Multi component Reaction Derived Acrylate Monomers", Macro Molecular Chemistry and Physics, vol. 222, No. 24, Nov. 8, 2021(Nov. 8, 2021), XP093137710, DE ISSN: 1022-1352, DOI: 10.1002/macp.202100328.

*Primary Examiner* — Michael F Pepitone
(74) *Attorney, Agent, or Firm* — Johnson & Johnson Surgical Vision, Inc.

(57) ABSTRACT

Disclosed are hydrophobic, acrylic materials having both high refractive index and a high Abbe number. The materials may have an internal wetting agent, are well suited for use as implantable ophthalmic devices, and have a refractive index which may be edited through application of energy. When used for an intraocular lens, the high refractive index allows for a thin lens which compresses to allow a small incision size.

21 Claims, No Drawings

(56) References Cited

U.S. PATENT DOCUMENTS

| | | |
|---|---|---|
| 7,169,874 B2 | 1/2007 | Salamone et al. |
| 7,217,778 B2 | 5/2007 | Verbruggen |
| 7,279,538 B2 | 10/2007 | Lai et al. |
| 7,295,749 B2 | 11/2007 | Kitamura et al. |
| 7,297,160 B2 | 11/2007 | Salamone et al. |
| 7,301,705 B2 | 11/2007 | Yoshimura et al. |
| 7,423,108 B2 | 9/2008 | Kunzler et al. |
| 7,632,904 B2 | 12/2009 | Salamone et al. |
| 7,714,090 B2 | 5/2010 | Iwamoto et al. |
| 7,763,682 B2 | 7/2010 | Lowery et al. |
| 7,767,779 B2 | 8/2010 | Jallouli et al. |
| 7,928,171 B2 | 4/2011 | Makker et al. |
| 8,148,445 B1 | 4/2012 | Laredo |
| 8,293,858 B1 | 10/2012 | Laredo |
| 8,323,799 B2 | 12/2012 | Hu et al. |
| 8,329,763 B2 | 12/2012 | Werner |
| 8,449,610 B2 | 5/2013 | Laredo et al. |
| 8,470,948 B2 | 6/2013 | Stiegman |
| 8,681,428 B1 | 3/2014 | Brown |
| 8,759,414 B2 | 6/2014 | Muller-Lierheim et al. |
| 9,012,566 B2 | 4/2015 | Buhler et al. |
| 9,289,531 B2 | 3/2016 | Jiang et al. |
| 9,427,493 B2 | 8/2016 | Kahook et al. |
| 9,475,967 B2 | 10/2016 | Lipscomb et al. |
| 9,622,853 B2 | 4/2017 | Argal |
| 9,820,850 B2 | 11/2017 | Mentak |
| 9,864,102 B2 | 1/2018 | Laredo et al. |
| 9,921,341 B2 | 3/2018 | Laredo et al. |
| 10,053,249 B2 | 8/2018 | Stutz et al. |
| 10,117,965 B1 | 11/2018 | Suganuma et al. |
| 10,155,349 B2 | 12/2018 | Pruitt et al. |
| 10,408,947 B2 | 9/2019 | Beacham et al. |
| 10,408,974 B2 | 9/2019 | Schlueter |
| 10,626,206 B2 | 4/2020 | Terrisse |
| 10,722,612 B2 | 7/2020 | Jiang et al. |
| 11,708,440 B2 * | 7/2023 | Alli .................. C08F 220/1806 523/108 |
| 2002/0049290 A1 | 4/2002 | Vanderbilt |
| 2004/0248038 A1 | 12/2004 | Yokoyama et al. |
| 2005/0254003 A1 | 11/2005 | Jani et al. |
| 2007/0004863 A1 | 1/2007 | Mentak |
| 2007/0222095 A1 | 9/2007 | Zanini et al. |
| 2007/0249794 A1 | 10/2007 | Evans et al. |
| 2008/0015282 A1 | 1/2008 | McCabe et al. |
| 2008/0200582 A1 | 8/2008 | Craciun et al. |
| 2011/0177256 A1 | 7/2011 | McAneney et al. |
| 2012/0202916 A1 | 8/2012 | Laredo et al. |
| 2012/0309919 A1 | 12/2012 | Laredo |
| 2013/0253159 A1 | 9/2013 | Benz et al. |
| 2013/0345364 A1 | 12/2013 | Alli et al. |
| 2014/0163130 A1 | 6/2014 | Zhang et al. |
| 2015/0299500 A1 | 10/2015 | Haraguchi et al. |
| 2015/0321991 A1 | 11/2015 | Ponrathnam et al. |
| 2016/0235886 A1 | 8/2016 | Jiang et al. |
| 2017/0072601 A1 | 3/2017 | Akasaki et al. |
| 2018/0009922 A1 | 1/2018 | Alli et al. |
| 2018/0011222 A1 | 1/2018 | Alli et al. |
| 2018/0011223 A1 | 1/2018 | Alli et al. |
| 2018/0319901 A1 | 11/2018 | Hampson et al. |
| 2019/0000364 A1 | 1/2019 | Balaconis et al. |
| 2019/0225726 A1 | 7/2019 | DeSousa et al. |
| 2019/0314547 A1 | 10/2019 | Sui et al. |
| 2019/0338092 A1 | 11/2019 | Reit et al. |
| 2019/0339419 A1 | 11/2019 | Schlueter |
| 2020/0038548 A1 | 2/2020 | Suganuma et al. |
| 2020/0038549 A1 | 2/2020 | Stoy et al. |
| 2020/0123410 A1 | 4/2020 | Reit et al. |
| 2020/0165411 A1 | 5/2020 | Takagi et al. |
| 2020/0255709 A1 | 8/2020 | Reit et al. |
| 2020/0347166 A1 | 11/2020 | Alli et al. |
| 2020/0347167 A1 | 11/2020 | Alli et al. |
| 2022/0135720 A1 | 5/2022 | Alli et al. |
| 2023/0265230 A1 | 8/2023 | Alli et al. |

FOREIGN PATENT DOCUMENTS

| | | |
|---|---|---|
| CA | 2752046 A1 | 8/2010 |
| CA | 2802793 A1 | 2/2012 |
| CN | 102822217 A | 12/2012 |
| CN | 102140149 B | 3/2013 |
| CN | 109337591 A | 2/2019 |
| CN | 105985749 B | 6/2019 |
| CN | 105985750 B | 6/2019 |
| CN | 106459316 B | 3/2020 |
| CN | 111512227 A | 8/2020 |
| CN | 107429129 B | 9/2020 |
| CN | 109438614 B | 1/2021 |
| DE | 4010784 C2 | 11/1994 |
| EP | 1003795 B1 | 2/2004 |
| EP | 1400542 A1 | 3/2004 |
| EP | 2906970 B1 | 11/2016 |
| EP | 3458118 A1 | 3/2019 |
| EP | 3627212 A1 | 3/2020 |
| FR | 2774998 A1 | 8/1999 |
| JP | H05202346 A | 8/1993 |
| JP | H0726193 A | 1/1995 |
| JP | 2000281634 A | 10/2000 |
| JP | 2003137938 A | 5/2003 |
| JP | 2004075879 A | 3/2004 |
| JP | 2006126797 A | 5/2006 |
| JP | 2006328094 A | 12/2006 |
| JP | 2007016141 A | 1/2007 |
| JP | 2007077215 A | 3/2007 |
| JP | 2007091921 A | 4/2007 |
| JP | 2007169560 A | 7/2007 |
| JP | 2007186630 A | 7/2007 |
| JP | 2007262175 A | 10/2007 |
| JP | 2008163258 A | 7/2008 |
| JP | 2009227778 A | 10/2009 |
| JP | 2009256275 A | 11/2009 |
| JP | 2009255662 A | 11/2009 |
| JP | 2010121030 A | 6/2010 |
| JP | 2011038050 A | 2/2011 |
| JP | 2012052098 A | 3/2012 |
| JP | 2012082386 A | 4/2012 |
| JP | 2013010842 A | 1/2013 |
| JP | 2013234127 A | 11/2013 |
| JP | 2014506814 A | 3/2014 |
| JP | 2014515964 A | 7/2014 |
| JP | 2015524089 A | 8/2015 |
| JP | 2015524090 A | 8/2015 |
| JP | 2018506348 A | 3/2018 |
| KR | 20080023016 A | 3/2008 |
| KR | 20110109938 A | 10/2011 |
| WO | 9727223 A1 | 7/1997 |
| WO | 0011097 A1 | 3/2000 |
| WO | 0064956 A1 | 11/2000 |
| WO | 03022322 A2 | 3/2003 |
| WO | 2006043409 A1 | 4/2006 |
| WO | 2011125956 A1 | 10/2011 |
| WO | 2012004744 A2 | 1/2012 |
| WO | 2012167124 A1 | 12/2012 |
| WO | 2013048993 A1 | 4/2013 |
| WO | 2015016363 A1 | 2/2015 |
| WO | 2015068839 A1 | 5/2015 |
| WO | 2015132605 A1 | 9/2015 |
| WO | 2015170278 A1 | 11/2015 |
| WO | 2017072186 A1 | 5/2017 |
| WO | 2018212063 A1 | 11/2018 |
| WO | 2018229653 A1 | 12/2018 |
| WO | 2022090857 A1 | 5/2022 |

* cited by examiner

HIGH REFRACTIVE INDEX, HIGH ABBE COMPOSITIONS

CROSS-REFERENCE TO RELATED APPLICATIONS

This application is a continuation application of and claims priority to U.S. Non-Provisional application Ser. No. 16/861,032, filed Apr. 28, 2020, now U.S. Pat. No. 11,708,440, which claims priority to U.S. Provisional Patent Application No. 62/842,993, filed on May 3, 2019, the entire contents of which are hereby incorporated by reference.

FIELD OF THE DISCLOSURE

This disclosure is directed to compositions comprising reactive monomer mixtures, which when polymerized form an acrylic material having a high refractive index and a high Abbe number. These materials, which may have an editable refractive index, are designed for use in ophthalmic devices, such as intraocular implants or lenses.

BACKGROUND OF THE DISCLOSURE

Cataract surgery is commonly performed to replace the natural eye lens that has become opaque. Materials that are used to replace the natural crystalline lens must be soft and have excellent flexibility so that, once formed into a lens, they may be folded and passed through an incision which is typically about 2 mm. Furthermore, the material must have excellent transparency and little to no glistening. Having a high refractive index allows for a thinner lens to be used. A material with a high Abbe number demonstrates less dispersion. This, in turn, allows for improved optical results and less light scattering. Combining a high refractive index with a high Abbe number provides preferable optical characteristics for a material.

One of the first patents in this area, U.S. Pat. No. 4,573,998, to Mazzocco, discloses a deformable intraocular lens that can be rolled to fit through a relatively small incision. The deformable lens is inserted into the eye while it is held in its rolled configuration, then released inside the chamber of the eye. The elastic properties of the lens cause it to resume its molded shape after insertion into the eye. Mazzocco discloses polyurethane elastomers, silicone elastomers, hydrogel polymer compounds, organic or synthetic gel compounds and combinations thereof as suitable materials for the deformable lens.

Friction from inside the delivery device and physician force during delivery can damage the lens. To overcome this issue, some delivery devices are coated to provide extra lubricity. For example, U.S. Pat. No. 8,323,799, to Hu, discloses a soft, flexible highly lubricious coatings for polymeric IOL insertion cartridges that allow IOLs to be easily inserted through small bore cartridges suitable for use with small (less than 3 mm) incisions. While such coatings are helpful, there is a need to further reduce friction forces imposed on the lens during insertion.

Accordingly, there is a need for a material, with a relatively high refractive index and Abbe number, which can be used to form a flexible intraocular lens which can be simply rolled or folded into a configuration which will fit through a small incision. There is further need for such a material to have internal lubricity.

SUMMARY OF THE DISCLOSURE

In certain embodiments, the present disclosure relates a composition made by free radical polymerization of a reactive monomer mixture comprising:

(A) (i) at least one aromatic (meth)acrylate; (ii) at least one hydroxyalkyl (meth)acrylate; (iii) at least one polyamide; and (iv) at least one bis(2-hydroxypropyl (meth)acrylate) terminated polysiloxane crosslinking agent; wherein the composition exhibits a refractive index of at least 1.45 and an Abbe number of at least 39 ("Composition (A)"); or (B) (i) at least one aromatic (meth)acrylate; (ii) at least one hydroxyalkyl (meth)acrylate; and (iii) at least one bis(2-hydroxypropyl (meth)acrylate) terminated polysiloxane crosslinking agent; wherein the crosslinking agent is present in the reactive monomer mixture in an amount of about 15% to about 22% by weight ("Composition (B)"); or (C) (i) at least one hydrophobic monomer; (ii) at least one hydroxyl-containing monomer; (iii) at least one crosslinking agent; and (iv) at least one polyamide, wherein the reactive monomer mixture comprises the polyamide in an amount of about 0.10 to about 5.0 weight percent ("Composition (C)").

In certain embodiments, the present disclosure provides a device comprising Composition (A), Composition (B) or Composition (C). In certain other embodiments, the device is an ophthalmic device. In particular embodiments, the ophthalmic device comprises a lens, inlay, outlay, or insert selected from an intraocular implant or lens, a contact lens, a corneal inlay, a corneal outlay, and a corneal insert. In specific embodiments, the ophthalmic device is an intraocular implant or lens. More specifically, the present disclosure also provides intraocular implants and/or lenses made at least partially or completely from Composition (A), Composition (B) or Composition (C).

In still yet other embodiments, the present disclosure provides a method for making an ophthalmic device, the method comprising the steps of: (a) providing any one of Composition (A), Composition (B), or Composition (C); and (b) forming an ophthalmic device from any of said compositions. In other embodiments, the presently disclosed subject matter provides a method for making an ophthalmic device, the method comprising: (a) preparing a blank from any one of Composition (A), Composition (B), or Composition (C); and (b) machining an ophthalmic device from the blank. In other embodiments, the presently disclosed subject matter provides a method for making an ophthalmic device, the method comprising molding a lens from any one of Composition (A), Composition (B), or Composition (C); and (b) machining an ophthalmic device from the blank. In other embodiments, the presently disclosed subject matter provides a method for making an ophthalmic device, the method comprising molding a lens from any one of Composition (A), Composition (B), or Composition (C); and (b) machining the lens to refine the surface characteristics. In certain embodiments of either method, the method further comprises the step of extracting the ophthalmic device with a solvent. In certain embodiments, the method further comprises the step of hydrating the extracted ophthalmic device with at least one aqueous solution. In particular embodiments, the method further comprises an irradiation step using a laser. In more particular embodiments, the method further comprises a step of sterilizing the ophthalmic device.

DETAILED DESCRIPTION OF THE DISCLOSURE

It is to be understood that the disclosure is not limited to the details of construction or process steps set forth in the following description. The disclosure is capable of other embodiments and of being practiced or being carried out in various ways using the teaching herein.

A. Definitions

With respect to the terms used in this disclosure, the following definitions are provided.

Unless defined otherwise, all technical and scientific terms used herein have the same meaning as commonly understood by one of ordinary skill in the art to which the disclosure belongs. The polymer definitions are consistent with those disclosed in the Compendium of Polymer Terminology and Nomenclature, IUPAC Recommendations 2008, edited by: Richard G. Jones, Jaroslav Kahovec, Robert Stepto, Edward S. Wilks, Michael Hess, Tatsuki Kitayama, and W. Val Metanomski. All publications, patent applications, patents, and other references mentioned herein are incorporated by reference.

The term "reactive monomer mixture" refers to a mixture of components (both reactive and non-reactive) which are mixed together and when subjected to polymerization conditions, form the presently disclosed compositions and ophthalmic devices. The reactive mixture may include reactive components such as monomers, macromers, prepolymers, crosslinkers, initiators, diluents, and additional components, including, but not limited to, wetting agents, release agents, dyes, light absorbing compounds, such as UV absorbers, pigments, dyes and photochromic compounds, any of which may be reactive or non-reactive but are capable of being retained within the resulting biomedical device, e.g., an ophthalmic device, as well as active components, including pharmaceutical and nutraceutical compounds, and any diluents. It will be appreciated that a wide range of additives may be added based upon the biomedical device which is made, and its intended use. In some embodiments, concentrations of components of the reactive mixture are given in weight % of all components in the reaction mixture, excluding diluent. When diluents are used their concentrations are given as weight % based upon the amount of all components in the reaction mixture and the diluent.

"Reactive components" are the components in the reactive monomer mixture which become part of the structure of the polymeric network of the resulting composition, by covalent bonding or hydrogen bonding. Diluents and processing aids which do not become part of the structure of the polymer are not reactive components.

As used herein, the term "(meth)" designates optional methyl substitution. Thus, a term such as "(meth)acrylates" denotes both methacrylates and acrylates.

Wherever chemical structures are given, it should be appreciated that alternatives disclosed for the substituents on the structure may be combined in any combination. Thus, if a structure contained substituents R* and R**, each of which contained three lists of potential groups, 9 combinations are disclosed. The same applies for combinations of properties.

When a subscript, such as "n" in the generic formula [***]$_n$, is used to depict the number of repeating units in a polymer's chemical formula, the formula should be interpreted to represent the number average molecular weight of the macromolecule.

The term "individual" includes humans and non-human vertebrates.

The term "biomedical device" refers to any article that is designed to be used while either in or on mammalian tissues or fluids, and preferably in or on human tissue or fluids. Examples of these devices include but are not limited to wound dressings, sealants, tissue fillers, drug delivery systems, coatings, adhesion prevention barriers, catheters, implants, stents, and ophthalmic devices such as intraocular implants, intraocular lenses, and contact lenses. The biomedical devices may be ophthalmic devices, particularly ophthalmic implants or ophthalmic lenses made from the reactive monomer compositions described herein.

The term "ocular surface" includes the surface and glandular epithelia of the cornea, conjunctiva, lacrimal gland, accessory lacrimal glands, nasolacrimal duct and meibomian gland, and their apical and basal matrices, puncta and adjacent or related structures, including eyelids linked as a functional system by both continuity of epithelia, by innervation, and the endocrine and immune systems.

The term "ophthalmic device" refers to any device which resides in or on the eye or any part of the eye, including the ocular surface. These devices can provide optical correction, cosmetic enhancement, vision enhancement, therapeutic benefit (for example as bandages) or delivery of active components such as pharmaceutical and nutraceutical components, or a combination of any of the foregoing. Examples of ophthalmic devices include but are not limited to lenses, optical and ocular inserts, including but not limited to punctal plugs, and the like. "Lenses" include soft contact lenses, hard contact lenses, hybrid contact lenses, intraocular lenses, and overlay lenses. The ophthalmic device may comprise an intraocular implant, intraocular lens, or contact lens.

The term "contact lens" refers to an ophthalmic device that can be placed on the cornea of an individual's eye. The contact lens may provide corrective, cosmetic, or therapeutic benefit, including wound healing, the delivery of drugs or nutraceuticals, diagnostic evaluation or monitoring, ultraviolet light absorbing, visible light or glare reduction, or any combination thereof. A contact lens can be of any appropriate material known in the art and can be a soft lens, a hard lens, or a hybrid lens containing at least two distinct portions with different physical, mechanical, or optical properties, such as modulus, water content, light transmission, or combinations thereof.

"Intraocular lens" refers to a lens implanted in an eye. In some embodiments, the intraocular lens is implanted in the eye to replace an existing crystalline lens (such as, for example, because the existing lens has been clouded over by a cataract, or as a form of refractive surgery to change the eye's optical power).

"Target macromolecule" means the macromolecule being synthesized from the reactive monomer mixture comprising monomers, macromers, prepolymers, crosslinkers, initiators, additives, diluents, and the like.

The term "polymerizable compound" means a compound containing one or more polymerizable groups. The term encompasses, for instance, monomers, macromers, oligomers, prepolymers, crosslinkers, and the like.

"Polymerizable groups" are groups that can undergo chain growth polymerization, such as free radical and/or cationic polymerization, for example a carbon-carbon double bond which can polymerize when subjected to radical polymerization initiation conditions. Non-limiting examples of free radical polymerizable groups include (meth)acrylates, styrenes, vinyl ethers, (meth)acrylamides, N-vinyllactams, N-vinylamides, O-vinylcarbamates, O-vinylcarbonates, and other vinyl groups. Preferably, the free radical polymerizable groups comprise (meth)acrylate, (meth)acrylamide, N-vinyl lactam, N-vinylamide, and styryl functional groups, and mixtures of any of the foregoing. More preferably, the free radical polymerizable groups comprise (meth)acrylates, (meth)acrylamides, and mixtures thereof. The polymerizable group may be unsubstituted or substituted. For instance, the nitrogen atom in (meth)acrylamide may be bonded to a hydrogen, or the hydrogen may be replaced with alkyl or cycloalkyl (which themselves may be further substituted).

Any type of free radical polymerization may be used including but not limited to bulk, solution, suspension, and emulsion as well as any of the controlled radical polymerization methods such as stable free radical polymerization, nitroxide-mediated living polymerization, atom transfer radical polymerization, reversible addition fragmentation chain transfer polymerization, organotellurium mediated living radical polymerization, and the like.

A "monomer" is a mono-functional molecule which can undergo chain growth polymerization, and in particular, free radical polymerization, thereby creating a repeating unit in the chemical structure of the target macromolecule. Some monomers have di-functional impurities that can act as crosslinking agents. A "hydrophilic monomer" is also a monomer which yields a clear single phase solution when mixed with deionized water at 25° C. at a concentration of 5 weight percent. A "hydrophilic component" is a monomer, macromer, prepolymer, initiator, crosslinker, additive, or polymer which yields a clear single phase solution when mixed with deionized water at 25° C. at a concentration of 5 weight percent. A "hydrophobic component" is a monomer, macromer, prepolymer, initiator, crosslinker, additive, or polymer which is slightly soluble or insoluble in deionized water at 25° C.

A "macromolecule" is an organic compound having a number average molecular weight of greater than 1500 Daltons and may be reactive or non-reactive.

A "macromonomer" or "macromer" is a macromolecule that has one group that can undergo chain growth polymerization, and in particular, free radical polymerization, thereby creating a repeating unit in the chemical structure of the target macromolecule. Typically, the chemical structure of the macromer is different than the chemical structure of the target macromolecule, that is, the repeating unit of the macromer's pendent group is different than the repeating unit of the target macromolecule or its mainchain. The difference between a monomer and a macromer is merely one of chemical structure, molecular weight, and molecular weight distribution of the pendent group. As a result, and as used herein, the patent literature occasionally defines monomers as polymerizable compounds having relatively low molecular weights of about 1,500 daltons or less, which inherently includes some macromers. In particular, monomethacryloxypropyl terminated mono-n-butyl terminated polydimethylsiloxane (molecular weight=500-1500 g/mol) (mPDMS) and mono-(2-hydroxy-3-methacryloxy-propyl)-propyl ether terminated mono-n-butyl terminated polydimethylsiloxane (molecular weight=500-1500 g/mol) (OH-mPDMS) may be referred to as monomers or macromers. Furthermore, the patent literature occasionally defines macromers as having one or more polymerizable groups, essentially broadening the common definition of macromer to include prepolymers. As a result and as used herein, di-functional and multi-functional macromers, prepolymers, and crosslinkers may be used interchangeably.

A "polymer" is a target macromolecule composed of the repeating units of the monomers used during polymerization.

A "homopolymer" is a polymer made from one monomer; a "copolymer" is a polymer made from two or more monomers; a "terpolymer" is a polymer made from three monomers. A "block copolymer" is composed of compositionally different blocks or segments. Diblock copolymers have two blocks. Triblock copolymers have three blocks. "Comb or graft copolymers" are made from at least one macromer.

A "repeating unit" is the smallest group of atoms in a polymer that corresponds to the polymerization of a specific monomer or macromer.

An "initiator" is a molecule that can decompose into radicals which can subsequently react with a monomer to initiate a free radical polymerization reaction. A thermal initiator decomposes at a certain rate depending on the temperature; typical examples are azo compounds such as 1,1'-azobisisobutyronitrile and 4,4'-azobis(4-cyanovaleric acid), peroxides such as benzoyl peroxide, tert-butyl peroxide, tert-butyl hydroperoxide, tert-butyl peroxybenzoate, dicumyl peroxide, and lauroyl peroxide, peracids such as peracetic acid and potassium persulfate as well as various redox systems. A photo-initiator decomposes by a photochemical process; typical examples are derivatives of benzil, benzoin, acetophenone, benzophenone, camphorquinone, and mixtures thereof as well as various monoacyl and bisacyl phosphine oxides and combinations thereof.

A "crosslinking agent" is a di-functional or multi-functional monomer or macromer which can undergo free radical polymerization at two or more locations on the molecule, thereby creating branch points and a polymeric network. Common examples are ethylene glycol dimethacrylate, tetraethylene glycol dimethacrylate, trimethylolpropane trimethacrylate, methylene bisacrylamide, triallyl cyanurate, and the like.

A "prepolymer" is a reaction product of monomers which contains remaining polymerizable groups capable of undergoing further reaction to form a polymer. The terms "reactive mixture" and "reactive monomer mixture" refer to the mixture of components (both retained and non-retained) which are mixed together and, when subjected to polymerization conditions, result in formation of a polymeric network as well as biomedical devices, ophthalmic devices, intraocular implants, contact lenses, and intraocular lenses made therefrom. The reactive mixture may comprise retained components such as monomers, macromers, prepolymers, crosslinkers, and initiators, additives such as wetting agents, polymers, dyes, light absorbing compounds such as UV absorbers, pigments, photochromic compounds, pharmaceutical compounds, and/or nutraceutical compounds, any of which may be reactive or non-reactive but are capable of being retained within the resulting biomedical device. The reactive mixture may also contain non-retained components which are intended to be removed from the device prior to its use, such as diluents. It will be appreciated that a wide range of additives may be added based upon the biomedical device which is made and its intended use. Concentrations of components of the reactive mixture are expressed as weight percentages of all retained components in the reactive mixture, therefore excluding non-retained components such as diluent. When diluents are used, their concentrations are expressed as weight percentages based upon the amount of all components in the reactive mixture (including the diluent).

"Retained components" are the polymerizable compounds (such as monomers, macromers, oligomers, prepolymers, and crosslinkers) in the reactive mixture, as well as any other components in the reactive mixture which are intended to substantially remain in the polymeric network after polymerization and all work-up steps (such as extraction steps) and packaging steps have been completed. Retained components may be retained in the polymeric network by covalent bonding, hydrogen bonding, electrostatic interactions, the formation of interpenetrating polymeric networks, or any other means. Components that are intended to release from the biomedical device once it is in use are still considered "retained components." For example, pharmaceutical or nutraceutical components in a contact lens which are intended to be released during wear are considered "retained components." Components that are intended to be removed from the polymeric network during the manufacturing process (e.g., by extraction), such as diluents, are "non-retained components."

The term "multi-functional" refers to a component having two or more polymerizable groups. The term "mono-functional" refers to a component having one polymerizable group.

The terms "halogen" or "halo" indicate fluorine, chlorine, bromine, and iodine.

"Alkyl" or "aliphatic" are used interchangeably herein and refer to an optionally substituted linear or branched alkyl group containing the indicated number of carbon atoms. If no number is indicated, then alkyl (including any optional substituents on alkyl) may contain 1 to 16 carbon atoms, including 1, 2, 3, 4, 5, 6, 7, 8, 9, 10, 11, 12, 13, 14, 15, and 16 carbon atoms. Preferably, the alkyl group contains 1 to 10 carbon atoms, including 1, 2, 3, 4, 5, 6, 7, 8, 9, and 10 carbon atoms, alternatively 1 to 8 carbon atoms, including 1, 2, 3, 4, 5, 6, 7, and 8 carbon atoms, alternatively 1 to 6 carbon atoms, including 1, 2, 3, and 4 carbon atoms, or alternatively 1 to 4 carbon atoms, including 1, 2, 3, and 4. Examples of alkyl include methyl, ethyl, propyl, isopropyl, butyl, iso-, sec- and tert-butyl, pentyl, hexyl, heptyl, 3-ethylbutyl, and the like.

Examples of substituents on alkyl include 1, 2, or 3 groups independently selected from hydroxy, amino, amido, oxa, carboxy, alkyl carboxy, carbonyl, alkoxy, thioalkyl, carbamate, carbonate, halogen, phenyl, benzyl, and combinations thereof. "Alkylene" means a divalent alkyl group, such as —$CH_2$—, —$CH_2CH_2$—, —$CH_2CH_2CH_2$—, —$CH_2CH(CH_3)CH_2$—, and —$CH_2CH_2CH_2CH_2$—.

"Haloalkyl" refers to an alkyl group as defined above substituted with one or more halogen atoms, where each halogen is independently F, Cl, Br or I. A preferred halogen is F. Preferred haloalkyl groups contain 1-6 carbons, more preferably 1-4 carbons, and still more preferably 1-2 carbons. "Haloalkyl" includes perhaloalkyl groups, such as —$CF_3$— or —$CF_2CF_3$—. "Haloalkylene" means a divalent haloalkyl group, such as —$CH_2CF_2$—.

"Hydroxy" refers to an —OH group.

"Hydroxyalkyl" refers to an alkyl group, as defined herein, substituted with at least one hydroxy group. Representative examples of hydroxyalkyl include, but are not limited to, hydroxymethyl, 2-hydroxyethyl, 3-hydroxypropyl, 2,3-dihydroxypropyl, 2,3-dihydroxypentyl, 4-hydroxybutyl, 2-ethyl-4-hydroxyheptyl, 3,4-dihydroxybutyl, and 5-hydroxypentyl.

"Cycloalkyl" or "cycloaliphatic" are used interchangeably herein and refer to an optionally substituted cyclic hydrocarbon containing the indicated number of ring carbon atoms. If no number is indicated, then cycloalkyl may contain 3 to 12 ring carbon atoms. Preferred are $C_3$-$C_8$ cycloalkyl groups, $C_3$-$C_7$ cycloalkyl, more preferably $C_4$-$C_7$ cycloalkyl, and still more preferably $C_5$-$C_6$ cycloalkyl. Examples of cycloalkyl include cyclopropyl, cyclobutyl, cyclopentyl, cyclohexyl, cycloheptyl and cyclooctyl. Examples of substituents on cycloalkyl include 1, 2, or 3 groups independently selected from alkyl, hydroxy, amino, amido, oxa, carbonyl, alkoxy, thioalkyl, amido, carbamate, carbonate, halo, phenyl, benzyl, and combinations thereof.

"Cycloalkylene" means a divalent cycloalkyl group, such as 1,2-cyclohexylene, 1,3-cyclohexylene, or 1,4-cyclohexylene.

"Heterocycloalkyl" refers to a cycloalkyl ring or ring system as defined above in which at least one ring carbon has been replaced with a heteroatom selected from nitrogen, oxygen, and sulfur. The heterocycloalkyl ring is optionally fused to or otherwise attached to other heterocycloalkyl rings and/or non-aromatic hydrocarbon rings and/or phenyl rings. Preferred heterocycloalkyl groups have from 5 to 7 members. More preferred heterocycloalkyl groups have 5 or 6 members. Heterocycloalkylene means a divalent heterocycloalkyl group.

"Aryl" refers to an optionally substituted aromatic hydrocarbon ring system containing at least one aromatic ring. The aryl group contains the indicated number of ring carbon atoms. If no number is indicated, then aryl may contain 6 to 14 ring carbon atoms. The aromatic ring may optionally be fused or otherwise attached to other aromatic hydrocarbon rings or non-aromatic hydrocarbon rings. Examples of aryl groups include phenyl, naphthyl, and biphenyl. Preferred examples of aryl groups include phenyl. Examples of substituents on aryl include 1, 2, or 3 groups independently selected from alkyl, hydroxy, amino, amido, oxa, carboxy, alkyl carboxy, carbonyl, alkoxy, thioalkyl, carbamate, carbonate, halo, phenyl, benzyl, and combinations thereof. "Arylene" means a divalent aryl group, for example 1,2-phenylene, 1,3-phenylene, or 1,4-phenylene.

"Arylalkyl" refers to an aryl group, as defined herein, appended to the parent molecular moiety through an alkyl group, as defined herein. Representative examples of arylalkyl include phenylmethyl (i.e. benzyl), 2-phenylethyl, 3-phenylpropyl, and 4-phenylbutyl.

"Heteroaryl" refers to an aryl ring or ring system, as defined above, in which at least one ring carbon atom has been replaced with a heteroatom selected from nitrogen, oxygen, and sulfur. The heteroaryl ring may be fused or otherwise attached to one or more heteroaryl rings, aromatic or nonaromatic hydrocarbon rings or heterocycloalkyl rings. Examples of heteroaryl groups include pyridyl, furyl, and thienyl. "Heteroarylene" means a divalent heteroaryl group.

"Alkoxy" refers to an alkyl group attached to the parent molecular moiety through an oxygen bridge. Examples of alkoxy groups include, for instance, methoxy, ethoxy, propoxy and isopropoxy. "Thioalkyl" means an alkyl group attached to the parent molecule through a sulfur bridge. Examples of thioalkyl groups include, for instance, methylthio, ethylthio, n-propylthio and iso-propylthio. "Aryloxy" refers to an aryl group attached to a parent molecular moiety through an oxygen bridge. Examples include phenoxy. "Arylthio" refers to an aryl group attached to a parent molecular moiety through a sulfur bridge. Examples include phenylthiol. "Cyclic alkoxy" means a cycloalkyl group attached to the parent moiety through an oxygen bridge.

"Alkylamine" refers to an alkyl group attached to the parent molecular moiety through an —NH bridge. Alkyleneamine means a divalent alkylamine group, such as —$CH_2CH_2NH$—.

"Siloxanyl" refers to a structure having at least one Si—O—Si bond. Thus, for example, siloxanyl group means a group having at least one Si—O—Si group (i.e. a siloxane group), and siloxanyl compound means a compound having at least one Si—O—Si group. "Siloxanyl" encompasses monomeric (e.g., Si—O—Si) as well as oligomeric/polymeric structures (e.g., —[Si—O]$_n$—, where n is 2 or more). Each silicon atom in the siloxanyl group is substituted with independently selected $R^A$ groups (where $R^A$ is as defined in formula A options (b)-(i)) to complete their valence.

Formula A. The silicone-containing component may comprise one or more polymerizable compounds of Formula A:

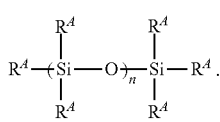

Formula A wherein:
at least one $R^A$ is a group of formula $R_g$-L- wherein $R_g$ is a polymerizable group and L is a linking group, and the remaining $R^A$ are each independently:
a. $R_g$-L-,
b. $C_1$-$C_{16}$ alkyl optionally substituted with one or more hydroxy, amino, amido, oxa, carboxy, alkyl carboxy, carbonyl, alkoxy, amido, carbamate, carbonate, halo, phenyl, benzyl, or combinations thereof,
c. $C_3$-C12 cycloalkyl optionally substituted with one or more alkyl, hydroxy, amino, amido, oxa, carbonyl, alkoxy, amido, carbamate, carbonate, halo, phenyl, benzyl, or combinations thereof,
d. a C6-C14 aryl group optionally substituted with one or more alkyl, hydroxy, amino, amido, oxa, carboxy, alkyl carboxy, carbonyl, alkoxy, amido, carbamate, carbonate, halo, phenyl, benzyl, or combinations thereof,
e. halo,
f. alkoxy, cyclic alkoxy, or aryloxy,
g. siloxy,
h. alkyleneoxy-alkyl or alkoxy-alkyleneoxy-alkyl, such as polyethyleneoxyalkyl, polypropyleneoxyalkyl, or poly(ethyleneoxy-co-propyleneoxyalkyl), or
a monovalent siloxane chain comprising from 1 to 100 siloxane repeat units optionally substituted with alkyl, alkoxy, hydroxy, amino, oxa, carboxy, alkyl carboxy, alkoxy, amido, carbamate, halo or combinations thereof, and
n is from 0 to 500 or from 0 to 200, or from 0 to 100, or from 0 to 20, where it is understood that when n is other than 0, n is a distribution having a mode equal to a stated value. When n is 2 or more, the SiO units may carry the same or different $R^A$ substituents and if different $R^A$ substituents are present, the n groups may be in random or block configuration.

In Formula A, three $R^A$ may each comprise a polymerizable group, alternatively two $R^A$ may each comprise a polymerizable group, or alternatively one $R^A$ may comprise a polymerizable group.

"Silyl" refers to a structure of formula $R_3Si$— and "siloxy" refers to a structure of formula $R_3Si$—O—, where each R in silyl or siloxy is independently selected from trimethylsiloxy, $C_1$-$C_8$ alkyl (preferably $C_1$-$C_3$ alkyl, more preferably ethyl or methyl), and $C_3$-$C_8$ cycloalkyl.

"Alkyleneoxy" refers to groups of the general formula -(alkylene-O)$_p$— or —(O-alkylene)$_p$-, wherein alkylene is as defined above, and p is from 1 to 200, or from 1 to 100, or from 1 to 50, or from 1 to 25, or from 1 to 20, or from 1 to 10, wherein each alkylene is independently optionally substituted with one or more groups independently selected from hydroxyl, halo (e.g., fluoro), amino, amido, ether, carbonyl, carboxyl, and combinations thereof. If p is greater than 1, then each alkylene may be the same or different and the alkyleneoxy may be in block or random configuration.

When alkyleneoxy forms a terminal group in a molecule, the terminal end of the alkyleneoxy may, for instance, be a hydroxy or alkoxy (e.g., HO—[CH$_2$CH$_2$O]$_p$— or CH$_3$O—[CH$_2$CH$_2$O]$_p$—). Examples of alkyleneoxy include polyethyleneoxy, polypropyleneoxy, polybutyleneoxy, and poly (ethyleneoxy-co-propyleneoxy).

"Oxaalkylene" refers to an alkylene group as defined above where one or more non-adjacent CH$_2$ groups have been substituted with an oxygen atom, such as —CH$_2$CH$_2$OCH(CH$_3$)CH$_2$—. "Thiaalkylene" refers to an alkylene group as defined above where one or more non-adjacent CH$_2$ groups have been substituted with a sulfur atom, such as —CH$_2$CH$_2$SCH(CH$_3$)CH$_2$—.

The term "linking group" refers to a moiety that links a polymerizable group to the parent molecule. The linking group may be any moiety that is compatible with the compound of which it is a part, and that does not undesirably interfere with the polymerization of the compound, is stable under the polymerization conditions as well as the conditions for the processing and storage of the final product. For instance, the linking group may be a bond, or it may comprise one or more alkylene, haloalkylene, amide, amine, alkyleneamine, carbamate, ester (—CO$_2$—), arylene, heteroarylene, cycloalkylene, heterocycloalkylene, alkyleneoxy, oxaalkylene, thiaalkylene, haloalkyleneoxy (alkyleneoxy substituted with one or more halo groups, e.g., —OCF$_2$—, —OCF$_2$CF$_2$—, —OCF$_2$CH$_2$—), siloxanyl, alkylenesiloxanyl, or combinations thereof. The linking group may optionally be substituted with 1 or more substituent groups. Suitable substituent groups may include those independently selected from alkyl, halo (e.g., fluoro), hydroxyl, HO-alkyleneoxy, MeO-alkyleneoxy, siloxanyl, siloxy, siloxy-alkyleneoxy-, siloxy-alkylene-alkyleneoxy- (where more than one alkyleneoxy groups may be present and wherein each methylene in alkylene and alkyleneoxy is independently optionally substituted with hydroxyl), ether, amine, carbonyl, carbamate, and combinations thereof. The linking group may also be substituted with a polymerizable group, such as (meth)acrylate (in addition to the polymerizable group to which the linking group is linked).

Preferred linking groups include $C_1$-$C_8$ alkylene (preferably $C_2$-$C_6$ alkylene) and $C_1$-$C_8$ oxaalkylene (preferably $C_2$-$C_6$ oxaalkylene), each of which is optionally substituted with 1 or 2 groups independently selected from hydroxyl and siloxy. Preferred linking groups also include carboxylate, amide, $C_1$-$C_8$ alkylene-carboxylate-$C_1$-$C_8$ alkylene, or $C_1$-$C_8$ alkylene-amide-$C_1$-$C_8$ alkylene.

When the linking group is comprised of combinations of moieties as described above (e.g., alkylene and cycloalkylene), the moieties may be present in any order. For instance, if in Formula A above, L is indicated as being -alkylene-cycloalkylene-, then Rg-L may be either Rg-alkylene-cycloalkylene-, or Rg-cycloalkylene-alkylene-. Notwithstanding this, the listing order represents the preferred order in which the moieties appear in the compound starting from the terminal polymerizable group (Rg or Pg) to which the linking group is attached. For example, if in Formula A, L is indicated as being alkylene-cycloalkylene, then Rg-L is preferably Rg-alkylene-cycloalkylene-.

The term "electron withdrawing group" (EWG) refers to a chemical group which withdraws electron density from the atom or group of atoms to which the electron withdrawing group is attached. Examples of EWGs include, but are not limited to, cyano, amide, ester, keto, or aldehyde. A preferred EWG is cyano (CN).

The terms "light absorbing compound" refers to a chemical material that absorbs light within the visible spectrum (e.g., in the 380 to 780 nm range). A "high energy radiation absorber," "UV/HEV absorber," or "high energy light absorbing compound" is a chemical material that absorbs various wavelengths of ultraviolet light, high energy visible light, or both. A material's ability to absorb certain wavelengths of light can be determined by measuring its UV/Vis transmission spectrum. Compounds that exhibit no absorption at a particular wavelength will exhibit substantially 100 percent transmission at that wavelength. Conversely, compounds that completely absorb at a particular wavelength will exhibit substantially 0% transmission at that wavelength. If the amount of a material's transmission is indicated as a percentage for a particular wavelength range, it is to be understood that the material exhibits the percent transmission at all wavelengths within that range.

When the compounds described herein contain olefinic double bonds or other centers of geometric asymmetry, and unless otherwise specified, it is intended that the compounds include the cis, trans, Z- and E- configurations. Likewise, all tautomeric and salt forms are also intended to be included.

The term "optional substituent" means that a hydrogen atom in the underlying moiety is optionally replaced by a substituent. Any substituent may be used that is sterically practical at the substitution site and is synthetically feasible. Identification of a suitable optional substituent is well within the capabilities of an ordinarily skilled artisan. Examples of an "optional substituent" include, without limitation, $C_1$-$C_6$ alkyl, $C_1$-$C_6$ alkoxy, $C_1$-$C_6$ thioalkyl, $C_3$-$C_7$ cycloalkyl, aryl, halo, hydroxy, amino, $NR^4R^5$, benzyl, $SO_3H$, or $SO_3Na$, wherein $R^4$ and $R^5$ are independently H or $C_1$-$C_6$ alkyl. The foregoing substituents may be optionally substituted by an optional substituent (which, unless otherwise indicated, is preferably not further substituted). For instance, alkyl may be substituted by halo (resulting, for instance, in $CF_3$).

Unless otherwise indicated, ratios, percentages, parts, and the like are by weight.

Unless otherwise indicated, numeric ranges, for instance as in "from 2 to 10," are inclusive of the numbers defining the range (e.g., 2 and 10).

In some embodiments, the reactive monomer mixture includes at least one polyamide. As used herein, the term "polyamide" refers to polymers and copolymers comprising repeating units containing amide groups. The polyamide may comprise cyclic amide groups, acyclic amide groups and combinations thereof, and may be any polyamide known to those of skill in the art. Acyclic polyamides comprise pendant acyclic amide groups and are capable of association with hydroxyl groups. Cyclic polyamides comprise cyclic amide groups and are capable of association with hydroxyl groups. Polyamides suitable for use with the presently disclosed compositions and methods are disclosed in U.S. Patent Application Publication No. 20180009922 for SILICONE HYDROGELS COMPRISING HIGH LEVELS OF POLYAMIDES to Alli et al., published Jan. 11, 2018, and U.S. Patent Application Publication No. 20180011222 for SILICONE HYDROGELS COMPRISING POLYAMIDES to Alli et al., published Jan. 11, 2018, each of which are incorporated herein by reference in their entirety.

"Abbe number," also known as the V-number or constringence of a transparent material, is a measure of the material's dispersion, i.e., variation of refractive index versus wavelength, with high values of V indicating low dispersion. The Abbe number, of a material is defined as:

$$V_D = \frac{n_D - 1}{n_F - n_C};$$

where $n_D$, $n_F$ and $n_C$ are the refractive indices of the material at the wavelengths of the Fraunhofer D-, F- and C- spectral lines (589.3 nm, 486.1 nm and 656.3 nm respectively).

"Refractive index" is defined as:

$$n = \frac{c}{v};$$

where c is the speed of light in a vacuum and v is the phase velocity of light in the medium.

B. Compositions

In some embodiments, the presently disclosed subject matter provides a composition made by free radical polymerization of a reactive monomer mixture comprising:

(A) (i) at least one aromatic (meth)acrylate; (ii) at least one hydroxyalkyl (meth)acrylate; (iii) at least one polyamide; and (iv) at least one bis(2-hydroxypropyl (meth)acrylate) terminated polysiloxane crosslinking agent; wherein the composition exhibits a refractive index of at least 1.45 and an Abbe number of at least 39 (hereinafter "Composition (A)"); or (B) (i) at least one aromatic (meth)acrylate; (ii) at least one hydroxyalkyl (meth)acrylate; and (iii) at least one bis(2-hydroxypropyl (meth)acrylate) terminated polysiloxane crosslinking agent; wherein the crosslinking agent is present in the reactive monomer mixture in an amount of about 15% to about 22% by weight (hereinafter "Composition (B)"); or (C) (i) at least one hydrophobic monomer; (ii) at least one hydroxyl-containing monomer; (iii) at least one crosslinking agent; and (iv) at least one polyamide, wherein the reactive monomer mixture comprises the polyamide in an amount of about 0.10 to about 5.0 weight percent (hereinafter "Composition (C)").

Each of the compositions will now be described in more detail.

1. Composition (A)

In some embodiments, the presently disclosed subject matter provides a composition, referred to herein as "Composition (A)," made by free radical polymerization of a reactive monomer mixture comprising: (a) at least one aromatic (meth)acrylate; (b) at least one hydroxyalkyl (meth)acrylate; (c) at least one polyamide; and (d) at least one bis(2-hydroxypropyl (meth)acrylate) terminated polysiloxane crosslinking agent; wherein the composition exhibits a refractive index of at least 1.45 and an Abbe number of at least 39.

In some embodiments of Composition (A), the at least one aromatic (meth)acrylate is a (meth)acrylate comprising at least one aryl group. In some embodiments, the aryl group is a phenyl group. In some embodiments, the aryl group is present in the aromatic (meth)acrylate as part of an arylalkyl group (e.g., benzyl, 2-phenylethyl, 3-phenylpropyl, or 4-phenylbutyl), an aryloxyalkyl group (e.g., phenoxymethyl, 2-phenoxyethyl, 3-phenoxypropyl, or 4-phenoxybutyl), or an arylthioalkyl group (e.g., phenylthiomethyl, 2-phenylthioethyl, 3-phenylthiopropyl, 4-phenylthiobutyl, or 1,3-bis(phenylthio)-2-propyl). In some embodiments, the at least one aromatic (meth)acrylate is selected from 2-phenylethyl (meth)acrylate, 2-phenoxyethyl (meth)acrylate, 3-phenylpropyl (meth)acrylate, 3-phenoxypropyl (meth)acrylate, 1,3-bis(phenylthio)-2-propyl (meth)acrylate, poly(ethylene glycol) phenyl ether (meth)acrylate, and any combination thereof. In some embodiments, the at least one aromatic (meth)acrylate is selected from 2-phenylethyl acrylate, 2-phenylethyl methacrylate, and 1,3-bis(phenylthio)-2-propyl acrylate. In some embodiments, the at least one aromatic (meth)acrylate is 2-phenylethyl acrylate. In some embodiments, the at least one aromatic (meth)acrylate is 2-phenylethyl methacrylate. In some embodiments, the at least one aromatic (meth)acrylate is 1,3-bis(phenylthio)-2-propyl acrylate.

In some embodiments of Composition (A), the at least one hydroxyalkyl (meth)acrylate comprises a linear, branched, or cyclic hydroxyalkyl group having between one and twenty-five carbon atoms, including 1, 2, 3, 4, 5, 6, 7, 8, 9, 10, 11, 12, 13, 14, 15, 16, 17, 18, 19, 20, 21, 22, 23, 24, and 25 carbon atoms. In particular embodiments, the at least one hydroxyalkyl (meth)acrylate is selected from 2-hydroxyethyl (meth)acrylate, 3-hydroxypropyl (meth)acrylate, 2-hydroxypropyl (meth)acrylate, 4-hydroxybutyl (meth)acrylate, and any combination thereof. In particular embodiments, the hydroxyalkyl (meth)acrylate is selected from 2-hydroxyethyl methacrylate and 4-hydroxybutyl acrylate. In some embodiments, the hydroxyalkyl (meth)acrylate is 2-hydroxyethyl methacrylate.

twenty-five carbon atoms, including 1, 2, 3, 4, 5, 6, 7, 8, 9, 10, 11, 12, 13, 14, 15, 16, 17, 18, 19, 20, 21, 22, 23, 24, and 25 carbon atoms, and the aryl group in each instance is benzyl, phenyl, or substituted phenyl. In particular embodiments, the at least one bis(2-hydroxypropyl (meth)acrylate) terminated polysiloxane crosslinking agent is a bis(2-hydroxypropyl (meth)acrylate) terminated poly(dimethylsiloxane).

In some embodiments, the reactive monomer mixture comprises the bis(2-hydroxypropyl (meth)acrylate) terminated poly(dimethylsiloxane) in an amount between about 15 weight percent and 30 weight percent, including about 15, 20, 25, and 30 weight percent. In some embodiments, the weight percent of the bis(2-hydroxypropyl (meth)acrylate) terminated poly(dimethylsiloxane) present in the reactive monomer mixture is calculated excluding a diluent.

In more certain embodiments, the at least one bis(2-hydroxypropyl (meth)acrylate) terminated polysiloxane crosslinking agent has formula:

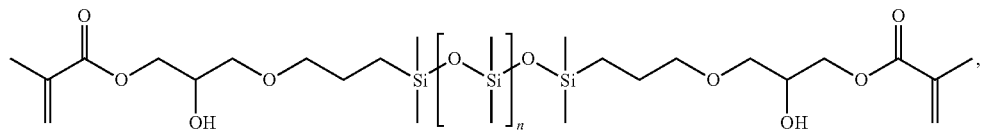

In some embodiments of Composition (A), the at least one polyamide is selected from poly(vinyl pyrrolidone), poly(N-vinyl-N-methyl acetamide), poly(N-vinyl acetamide), poly(dimethyl acrylamide), and a copolymer or a mixture thereof. In particular embodiments, the at least one polyamide is selected from poly(vinyl pyrrolidone) and poly(N-vinyl-N-methyl acetamide). In certain embodiments, the at least one polyamide is a copolymer.

In some embodiments, the reactive monomer mixture of Composition (A) comprises the at least one polyamide in an amount between about 0.1 weight percent and about 5 weight percent, including about 0.1, 0.5, 1, 2, 3, 4, and 5 weight percent, between about 0.5 weight percent and about 3 weight percent, including about 0.5, 1, 2, and 3 weight percent, or between about 0.5 weight percent and about 2 weight percent, including about 0.5, 1, and 2 weight percent. In some embodiments, the weight percent of the at least one polyamide present in the reactive monomer mixture is calculated excluding a diluent.

In some embodiments of Composition (A), the at least one bis(2-hydroxypropyl (meth)acrylate) terminated polysiloxane crosslinking agent is selected from a bis(2-hydroxypropyl (meth)acrylate) terminated poly(dialkylsiloxane), a bis(2-hydroxypropyl (meth)acrylate) terminated poly(diarylsiloxane), a bis(2-hydropropyl (meth)acrylate) terminated poly(dialkyl-co-diarylsiloxane), or any combination thereof, wherein the alkyl group in each instance is a linear, branched or cyclic hydrocarbon group containing between one and wherein n is an integer from 5 to 50, including 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50. In certain embodiments, n is an integer from 10 to 40. In certain embodiments, n is an integer from 15 to 30. In certain embodiments, n is an integer from 15 to 25. In certain embodiments, n is 15, 16, 17, 18, 19, 20, 21, 22, 23, 24, or 25. In yet more certain embodiments, n is 20.

In some embodiments, the Composition A is made by free radical polymerization of a reactive monomer mixture comprising: (a) at least one aromatic (meth)acrylate selected from 2-phenylethyl (meth)acrylate, 2-phenoxyethyl (meth)acrylate, 3-phenylpropyl (meth)acrylate, 3-phenoxypropyl (meth)acrylate, 1,3-bis(phenylthio)-2-propyl (meth)acrylate, poly(ethylene glycol) phenyl ether (meth)acrylate, and any combination thereof; (b) at least one hydroxyalkyl (meth)acrylate selected from 2-hydroxyethyl (meth)acrylate, 3-hydroxypropyl (meth)acrylate, 2-hydroxypropyl (meth)acrylate, 4-hydroxybutyl (meth)acrylate, and any combination thereof; (c) at least one polyamide selected from poly(vinyl pyrrolidone) and poly(N-vinyl-N-methyl acetamide); and (d) at least one bis(2-hydroxypropyl (meth)acrylate) terminated polysiloxane crosslinking agent having formula:

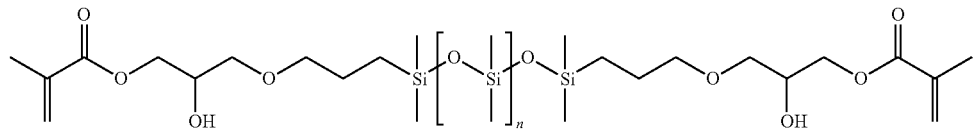

wherein n is an integer from 5 to 50 (e.g., 15 to 25);
wherein the composition exhibits a refractive index of at least 1.45 and an Abbe number of at least 39.

In some embodiments, Composition (A) further comprises at least one hydrophilic monomer. In certain embodiments, the at least one hydrophilic monomer is selected from vinyl pyrrolidone, N-vinyl-N-methyl acetamide, N-methyl methacrylamide, N-vinyl acetamide, N,N-dimethylacrylamide, poly(ethylene glycol) methyl ether methacrylate, poly(ethylene glycol) methacrylate, or any combination thereof.

In some embodiments, Composition (A) further comprises at least one hydroxy silicone monomer. In certain embodiments, the at least one hydroxy silicone monomer comprises mono-n-butyl terminated mono-(2-hydroxy-3-methacryloxypropyloxy)-propyl terminated polydimethylsiloxane, 3-(3-(1,1,1,3,5,5,5-heptamethyltrisiloxan-3-yl)propoxy)-2-hydroxypropyl methacrylate, 3-(3-(1,5-di-tert-butyl-1,1,3,5,5-pentamethyltrisiloxan-3-yl)propoxy)-2-hydroxypropyl methacrylate, or any combination thereof.

In some embodiments, Composition (A) further comprises at least one UV absorbing compound in the reactive monomer mixture. The UV absorbing compound may take the form of Formula I:

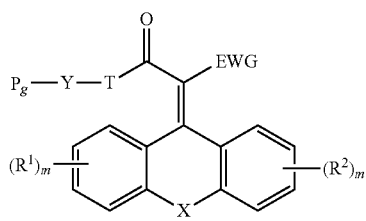

Formula I wherein:
m and n are independently 0, 1, 2, 3, or 4;
T is a bond, O, or NR;
X is O, S, NR, SO, or $SO_2$;
Y is a linking group;
$P_g$ is a polymerizable group;
R at each occurrence is independently H, $C_1$-$C_6$ alkyl, cycloalkyl, heterocycloalkyl, aryl, heteroaryl, or Y—$P_g$;
$R^1$ and $R^2$, when present, are independently at each occurrence $C_1$-$C_6$ alkyl, $C_1$-$C_6$ alkoxy, $C_1$-$C_6$ thioalkyl, $C_3$-$C_7$ cycloalkyl, aryl (preferably unsubstituted phenyl or phenyl substituted with alkyl or halo), halo, hydroxy, amino, $NR^3R^4$, or benzyl, wherein $R^3$ and $R^4$ are independently H or $C_1$-$C_6$ alkyl, or two adjacent $R^1$ or $R^2$ groups, together with the carbon atoms to which they are attached, combine to form a cycloalkyl or aryl ring; and
EWG is an electron withdrawing group.

Compounds of Formula I preferably contain one or two Y—$P_g$ groups. More preferably, the compounds contain one Y—Pg group.

In certain embodiments, the at least one UV absorbing compound comprises 2-(2'-hydroxy-5-methacrylyloxyethylphenyl)-2H-benzotriazole, 2-(2-cyano-2-(9H-thioxanthen-9-ylidene)acetamido)ethyl methacrylate, 2-(2-cyano-2-(9H-xanthen-9-ylidene)acetamido)ethyl methacrylate, 2-(2-cyano-2-(10-methylacridin-9(10H)-ylidene)acetamido)ethyl methacrylate or any combinations thereof. In certain embodiments, the at least one UV absorbing compound is 2-(2-cyano-2-(9H-thioxanthen-9-ylidene)acetamido)ethyl methacrylate.

In some embodiments, the reactive monomer mixture comprises the at least one UV absorbing compound in an amount between about 0.1 and about 5 weight percent, including about 0.1, 1, 2, 3, 4, and 5 weight percent, between about 1 and about 4 weight percent, including 1, 2, 3, and 4 weight percent, or between about 1 and about 3 weight percent, including about 1, 2, and 3 weight percent. In some embodiments, the weight percent of the at least one UV absorbing compound present in the reactive monomer mixture is calculated excluding a diluent.

In some embodiments, Composition (A) further comprises an unsaturated monomer having a polymerizable group and at least one other carbon-carbon double bond. In certain embodiments, the polymerizable group of the unsaturated monomer comprises a (meth)acrylate, a styrene, a vinyl ether, a (meth)acrylamide, an N-vinyllactam, an N-vinylamide, an O-vinylcarbamate, an O-vinylcarbonate, a vinyl group, or any combination thereof. In certain embodiments, the at least one other carbon-carbon double bond is present in a linear, branched or cyclic aliphatic hydrocarbon moiety having between two and thirty carbon atoms, including 2, 3, 4, 5, 6, 7, 8, 9, 10, 11, 12, 13, 14, 15, 16, 17, 18, 19, 20, 21, 22, 23, 24, 25, 26, 27, 28, 29, and 30 carbon atoms. In particular embodiments, the unsaturated monomer is selected from cyclohexenyl ether acrylate, N,N-diallyl acrylamide, diallyl maleate, allyl (meth)acrylate, 2-(allyloxy)ethyl (meth)acrylate, ((1R,2S,4R)-bicyclo[2.2.1]hept-5-en-2-yl)methyl (meth)acrylate, 2-(((3aS,4R,6S,7R,7aR)-3a,4,5,6,7,7a-hexahydro-1H-4,7-methanoinden-6-yl)oxy)ethyl (meth)acrylate (also known as ethylene glycol dicyclopentenyl ether (meth)acrylate), and any combination thereof.

In some embodiments, Composition (A) further comprises at least one diluent as defined herein in the reactive monomer mixture.

In some embodiments, Composition (A) has a water content of between about 0 weight percent and 15 weight percent, including about 0, 0.1, 0.5, 1, 2, 3, 4, 5, 6, 7, 8, 9, 10, 11, 12, 13, 14, and 15 weight percent, between about 0.5 weight percent and about 10 weight percent, including about 0.5, 1, 2, 3, 4, 5, 6, 7, 8, 9, and 10 weight percent, or between about 1 weight percent and about 8 weight percent, including about 1, 2, 3, 4, 5, 6, 7, and 8 weight percent.

In some embodiments, Composition (A) has a refractive index of at least 1.45 and an Abbe number of at least 45. In other embodiments, Composition (A) has a refractive index of at least 1.48 and an Abbe number of at least 50. In yet other embodiments, Composition (A) has a refractive index of at least 1.50 and an Abbe number of at least 50.

In some embodiments of Composition (A), the free radical polymerization is a photopolymerization using a bisacylphosphine oxide initiator. In some embodiments, the initiator is bis(2,4,6-trimethylbenzoyl)-phenylphosphineoxide.

2. Composition (B)

In some embodiments, the presently disclosed subject matter provides a composition, referred to herein as "Composition (B)," made by free radical polymerization of a reactive monomer mixture comprising: (a) at least one aromatic (meth)acrylate; (b) at least one hydroxyalkyl (meth)acrylate; and (c) at least one bis(2-hydroxypropyl) (meth)acrylate) terminated polysiloxane crosslinking agent; wherein the at least one bis(2-hydroxypropyl (meth)acrylate) terminated polysiloxane crosslinking agent is present in the reactive monomer mixture in an amount of about 15% to about 22% by weight, including about 15, 16, 17, 18, 19, 20, 21, and 22 weight percent, and any range encompassed between those amounts.

In some embodiments of Composition (B), the at least one aromatic (meth)acrylate is a (meth)acrylate comprising at least one aryl group. In some embodiments, the aryl group is a phenyl group. In some embodiments, the aryl group is present in the aromatic (meth)acrylate as part of an arylalkyl group (e.g., benzyl, 2-phenylethyl, 3-phenylpropyl, or 4-phenylbutyl), an aryloxyalkyl group (e.g., phenoxymethyl, 2-phenoxyethyl, 3-phenoxypropyl, or 4-phenoxybutyl), or an arylthioalkyl group (e.g., phenylthiomethyl, 2-phenylthioethyl, 3-phenylthiopropyl, or 4-phenylthiobutyl). In some embodiments, the at least one aromatic (meth)acrylate is selected from 2-phenylethyl (meth)acrylate, 2-phenoxyethyl (meth)acrylate, 4-chlorophenoxyethyl (meth)acrylate, 3-phenylpropyl (meth)acrylate, 3-phenoxypropyl (meth)acrylate, 1,3-bis-(phenylthio)-2-propyl (meth)acrylate, poly(ethylene glycol) phenyl ether (meth)acrylate, and any combination thereof. In certain embodiments, the at least one aromatic (meth)acrylate is 2-phenylethyl acrylate. In certain embodiments, the at least one aromatic (meth)acrylate is 2-phenylethyl methacrylate. In more certain embodiments, the at least one aromatic (meth)acrylate is a combination of 2-phenylethyl acrylate and 2-phenylethyl methacrylate.

In some embodiments, the reactive monomer mixture comprises the at least one aromatic (meth)acrylate in an amount between about 40 and about 80 weight percent, including about 40, 45, 50, 55, 60, 65, 70, 75, and 80 weight percent. In certain embodiments, the reactive monomer mixture comprises the at least one aromatic (meth)acrylate in an amount between about 60 and about 75 weight percent, including about 60, 65, 70, and 75 weight percent. In some embodiments, the weight percent of the at least one aromatic (meth)acrylate present in the reactive monomer mixture is calculated excluding a diluent.

In some embodiments of Composition (B), the at least one hydroxyalkyl (meth)acrylate is selected from 2-hydroxyethyl (meth)acrylate, 2-hydroxypropyl (meth)acrylate, 3-hydroxypropyl (meth)acrylate, 4-hydroxybutyl (meth)acrylate, and any combination thereof. In certain embodiments, the at least one hydroxyalkyl (meth)acrylate is 2-hydroxyethyl methacrylate or 4-hydroxybutyl acrylate. In some embodiments, the hydroxyalkyl (meth)acrylate is 2-hydroxyethyl methacrylate.

In some embodiments, the reactive monomer mixture comprises the at least one hydroxyalkyl (meth)acrylate in an amount between about 1 and about 20 weight percent, including about 1, 2, 3, 4, 5, 6, 7, 8, 9, 10, 11, 12, 13, 14, 15, 16, 17, 18, 19, and 20 weight percent. In certain embodiments, the reactive monomer mixture comprises the at least one hydroxyalkyl (meth)acrylate in an amount between about 5 and about 15 weight percent, including about 5, 6, 7, 8, 9, 10, 11, 12, 13, 14, and 15 weight percent. In some embodiments, the weight percent of the at least one hydroxyalkyl (meth)acrylate present in the reactive monomer mixture is calculated excluding a diluent.

In some embodiments of Composition (B), the at least one bis(2-hydroxypropyl (meth)acrylate) terminated polysiloxane crosslinking agent is selected from a bis(2-hydroxypropyl (meth)acrylate) terminated poly(dialkylsiloxane), a bis(2-hydroxypropyl (meth)acrylate) terminated poly(diarylsiloxane), a bis(2-hydropropyl (meth)acrylate) terminated poly(dialkyl-co-diarylsiloxane), or any combination thereof, wherein the alkyl group in each instance is a linear, branched or cyclic hydrocarbon group containing between one and twenty five carbon atoms, and the aryl group in each instance is benzyl, phenyl, or substituted phenyl.

In certain embodiments, the crosslinking agent is a bis (2-hydroxypropyl (meth)acrylate) terminated poly(dimethylsiloxane). In more certain embodiments, the at least one bis(2-hydroxypropyl (meth)acrylate) terminated polysiloxane crosslinking agent has formula:

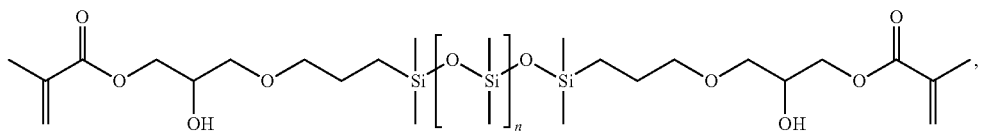

wherein n is an integer from 5 to 50, including 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50. In certain embodiments, n is an integer from 10 to 40. In certain embodiments, n is an integer from 15 to 30. In certain embodiments, n is an integer from 15 to 25. In certain embodiments, n is 15, 16, 17, 18, 19, 20, 21, 22, 23, 24, or 25. In yet more certain embodiments, n is 20.

In some embodiments, the reactive monomer mixture comprises the at least one bis(2-hydroxypropyl (meth)acrylate) terminated polysiloxane crosslinking agent in an amount of about 15% to about 22% by weight, including about 15, 16, 17, 18, 19, 20, 21, and 22% by weight. In certain embodiments, the reactive monomer mixture comprises the at least one bis(2-hydroxypropyl (meth)acrylate) terminated polysiloxane crosslinking agent in an amount of about 16% to about 20% by weight, including about 16, 17, 18, 19, and 20% by weight. In more certain embodiments, the reactive monomer mixture comprises the at least one bis(2-hydroxypropyl (meth)acrylate) terminated polysiloxane crosslinking agent in an amount of about 18% by weight. In some embodiments, the % by weight of the at least one bis(2-hydroxypropyl (meth)acrylate) terminated polysiloxane crosslinking agent present in the reactive monomer mixture is calculated excluding a diluent.

In some embodiments, the Composition (B) is made by free radical polymerization of a reactive monomer mixture comprising: (a) at least one aromatic (meth)acrylate selected from 2-phenylethyl (meth)acrylate, 2-phenoxyethyl (meth)acrylate, 3-phenylpropyl (meth)acrylate, 3-phenoxypropyl (meth)acrylate, 1,3-bis(phenylthio)-2-propyl (meth)acrylate, poly(ethylene glycol) phenyl ether (meth)acrylate, and any combination thereof; (b) at least one hydroxyalkyl (meth)acrylate selected from 2-hydroxyethyl (meth)acrylate, 3-hydroxypropyl (meth)acrylate, 2-hydroxypropyl (meth)acrylate, 4-hydroxybutyl (meth)acrylate, and any combination thereof, and (c) at least one bis(2-hydroxypropyl (meth)acrylate) terminated polysiloxane crosslinking agent having formula:

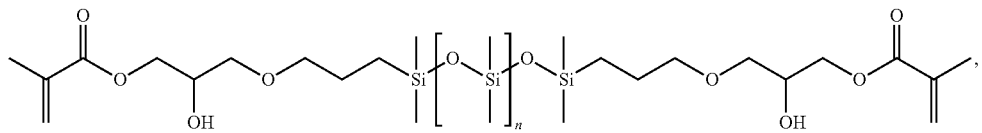

wherein n is an integer from 5 to 50 (e.g., 15 to 25); wherein the at least one bis(2-hydroxypropyl (meth)acrylate) terminated polysiloxane crosslinking agent is present in the reactive monomer mixture in an amount of about 15% to about 22% by weight, including about 15, 16, 17, 18, 19, 20, 21, and 22 weight percent, and any range encompassed between those amounts.

In some embodiments, Composition (B) further comprises a polyamide. In certain embodiments, the polyamide is selected from poly(vinyl pyrrolidone), poly(N-vinyl-N-methyl acetamide), poly(N-vinyl acetamide), poly(dimethyl acrylamide), and a copolymer or a mixture thereof. In certain embodiments, the polyamide is poly(N-vinyl-N-methyl acetamide). In certain embodiments, the polyamide is a copolymer.

In some embodiments, the reactive monomer mixture of Composition (B) comprises the polyamide in an amount between about 0.1 weight percent and about 5 weight percent, including about 0.1, 0.5, 1, 2, 3, 4, and 5 weight percent, between about 0.5 weight percent and about 3 weight percent, including about 0.5, 1, 2, and 3 weight percent, or between about 0.5 weight percent and about 2 weight percent, including about 0.5, 1, and 2 weight percent. In some embodiments, the weight percent of the polyamide present in the reactive monomer mixture is calculated excluding a diluent.

In some embodiments, Composition (B) further comprises at least one UV absorbing compound in the reactive monomer mixture. The UV absorbing compound may take the form of Formula I, above. In certain embodiments, the at least one UV absorbing compound is 2-(2'-hydroxy-5-methacrylyloxyethylphenyl)-2H-benzotriazole, 2-(2-cyano-2-(9H-thioxanthen-9-ylidene)acetamido)ethyl methacrylate, 2-(2-cyano-2-(9H-xanthen-9-ylidene)acetamido)ethyl methacrylate, 2-(2-cyano-2-(10-methylacridin-9(10H)-ylidene)acetamido)ethyl methacrylate, or any combination thereof. In certain embodiments, the at least one UV absorbing compound is 2-(2-cyano-2-(9H-thioxanthen-9-ylidene)acetamido)ethyl methacrylate.

In some embodiments, the reactive monomer mixture comprises the at least one UV absorbing compound in an amount between about 0.1 and about 5 weight percent, including about 0.1, 0.5, 1, 2, 3, 4, and 5 weight percent, between about 1 and about 4 weight percent, including about 1, 2, 3, and 4 weight percent, or between about 1 and about 3 weight percent, including about 1, 2, and 3 weight percent. In some embodiments, the weight percent of the at least one UV absorbing compound present in the reactive monomer mixture is calculated excluding a diluent.

In some embodiments, Composition (B) further comprises at least one diluent in the reactive monomer mixture.

In some embodiments, Composition (B) has a water content of between about 0 weight percent and about 15 weight percent, including about 0, 0.1, 0.5, 1, 2, 3, 4, 5, 6, 7, 8, 9, 10, 11, 12, 13, 14, and 15 weight percent, between about 1 weight percent and about 10 weight percent, including about 1, 2, 3, 4, 5, 6, 7, 8, 9, and 10 weight percent, or between about 1 weight percent and about 8 weight percent, including about 1, 2, 3, 4, 5, 6, 7, and 8 weight percent.

In some embodiments, Composition (B) has a refractive index of at least 1.45 and an Abbe number of at least 45. In other embodiments, Composition (B) has a refractive index of at least 1.48 and an Abbe number of at least 50. In yet other embodiments, Composition (B) has a refractive index of at least 1.50 and an Abbe number of at least 50.

In some embodiments of Composition (B), the free radical polymerization is a photopolymerization using a bisacylphosphine oxide initiator. In some embodiments, the initiator is bis(2,4,6-trimethylbenzoyl)-phenylphosphineoxide.

3. Composition (C)

In some embodiments, the presently disclosed subject matter provides a composition, referred to herein as "Composition (C)" made by free radical polymerization of a reactive monomer mixture comprising: (a) at least one hydrophobic monomer; (b) at least one hydroxyl-containing monomer; (c) at least one crosslinking agent; and (d) at least one polyamide, wherein the reactive monomer mixture comprises the at least one polyamide in an amount of about 0.10 to about 5.0 weight percent, including about 0.1, 0.5, 1, 2, 3, 4, and 5 weight percent. In some embodiments, the weight percent of the at least one polyamide present in the reactive monomer mixture is calculated excluding a diluent.

In some embodiments of Composition (C), the at least one hydrophobic monomer is a hydrophobic (meth)acrylate monomer. In certain embodiments, the hydrophobic (meth)acrylate is selected from an aliphatic (meth)acrylate, an aromatic (meth)acrylate, a cycloaliphatic (meth)acrylate, and any combination thereof. In more certain embodiments, the hydrophobic (meth)acrylate is an aliphatic (meth)acrylate. In particular embodiments, the aliphatic (meth)acrylate is a $C_1$-$C_{18}$ alkyl (meth)acrylate, including $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, and $C_{18}$ alkyl (meth)acrylate. In more particular embodiments, the $C_1$-$C_{18}$ alkyl (meth)acrylate is selected from the group consisting of ethyl (meth)acrylate, n-butyl (meth)acrylate, iso-butyl (meth)acrylate, t-butyl (meth)acrylate, n-hexyl (meth)acrylate, 2-ethylhexyl (meth)acrylate, octyl (meth)acrylate, iso-decyl (meth)acrylate, heptadecyl (meth)acrylate, dodecyl (meth)acrylate, 2-propylheptyl (meth)acrylate, stearyl (meth)acrylate, and any combination thereof. In yet more particular embodiments, the $C_1$-$C_{18}$ alkyl (meth)acrylate is n-hexyl acrylate.

In some embodiments of Composition (C), the hydrophobic (meth)acrylate is an aromatic (meth)acrylate. In certain embodiments, the at least one aromatic (meth)acrylate is a (meth)acrylate comprising at least one aryl group. In some embodiments, the aryl group is a phenyl group. In some embodiments, the aryl group is present in the aromatic (meth)acrylate as part of an arylalkyl group (e.g., benzyl, 2-phenylethyl, 3-phenylpropyl, or 4-phenylbutyl), an aryloxyalkyl group (e.g., phenoxymethyl, 2-phenoxyethyl, 3-phenoxypropyl, or 4-phenoxybutyl), or an arylthioalkyl group (e.g., phenylthiomethyl, 2-phenylthioethyl, 3-phenylthiopropyl, or 4-phenylthiobutyl). In some embodiments, the aromatic (meth)acrylate is selected from the group consisting of 2-phenylethyl (meth)acrylate, 2-phenoxyethyl (meth)acrylate, 4-chlorophenoxyethyl (meth)acrylate, 3-phenylpropyl (meth)acrylate, 3-phenoxypropyl (meth)acrylate, 1,3-bis-(phenylthio)-2-propyl (meth)acrylate, poly(ethylene glycol) phenyl ether (meth)acrylate, and any combination thereof. In certain embodiments, the aromatic (meth)acrylate is 2-phenylethyl acrylate. In certain embodiments, the aromatic (meth)acrylate is 2-phenylethyl methacrylate. In certain embodiments, the aromatic (meth)acrylate is a combination of 2-phenylethyl acrylate and 2-phenylethyl methacrylate.

In some embodiments of Composition (C), the hydrophobic (meth)acrylate is a cycloaliphatic (meth)acrylate. In some embodiments, the cycloaliphatic group has one cycloaliphatic ring. The cycloaliphatic ring may be a $C_3$-$C_8$ cycloalkyl group, a $C_3$-$C_7$ cycloalkyl group, a $C_4$-$C_7$ cycloalkyl group, or a $C_5$-$C_6$ cycloalkyl group. In some embodiments, the at least one cycloaliphatic (meth)acrylate has at least one cycloaliphatic group comprising at least one carbon-carbon double bond. In certain embodiments, the cycloaliphatic (meth)acrylate comprises cyclohexyl (meth)acrylate, cyclopentyl (meth)acrylate, 2-cyclohexylethyl (meth)acrylate, 3-cyclohexylpropyl (meth)acrylate, norbornyl (meth)acrylate, isobornyl (meth)acrylate, ((1R,2S,4R)-bicyclo[2.2.1]hept-5-en-2-yl)methyl (meth)acrylate, 2-(((3aS,4R,6S,7R,7aR)-3a,4,5,6,7,7a-hexahydro-1H-4,7-methanoinden-6-yl)oxy)ethyl (meth)acrylate (also known as ethylene glycol dicyclopentenyl ether (meth)acrylate), or any combination thereof. In some embodiments, the cycloaliphatic (meth)acrylate is selected from cyclohexyl acrylate, cyclohexylmethyl acrylate, 2-cyclohexylethylacrylate, 3-cyclohexylpropylacrylate, and ethylene glycol dicyclopentenyl ether acrylate. In some embodiments, the cycloaliphatic (meth)acrylate is selected from cyclohexyl acrylate, cyclohexylmethyl acrylate, 2-cyclohexylethylacrylate, and 3-cyclohexylpropylacrylate. In particular embodiments, the cycloaliphatic (meth)acrylate is cyclohexyl acrylate. In some embodiments, the cycloaliphatic (meth)acrylate is ethylene glycol dicyclopentenyl ether acrylate.

In some embodiments, Composition (C) comprises an aliphatic (meth)acrylate, an aromatic (meth)acrylate, and a cycloaliphatic (meth)acrylate. In particular embodiments, Composition (C) comprises cyclohexyl acrylate, phenylethyl acrylate, and n-hexyl acrylate.

In some embodiments of Composition (C), the reactive monomer mixture comprises the at least one hydrophobic monomer in an amount between about 50 and 90 weight percent, including 50, 55, 60, 65, 70, 75, 80, 85, and 90 weight percent. In some embodiments, the weight percent of the at least one hydrophobic monomer present in the reactive monomer mixture is calculated excluding a diluent.

In some embodiments of Composition (C), the at least one hydroxyl-containing monomer is a hydroxyalkyl (meth)acrylate. In certain embodiments, the hydroxyalkyl (meth)acrylate comprises 2-hydroxyethyl (meth)acrylate, 2-hydroxypropyl (meth)acrylate, 3-hydroxypropyl (meth)acrylate, 4-hydroxybutyl (meth)acrylate, or any combination thereof. In more certain embodiments, the hydroxyalkyl (meth)acrylate is 2-hydroxyethyl methacrylate or 4-hydroxybutyl acrylate. In some embodiments, the hydroxyalkyl (meth)acrylate is 2-hydroxyethyl methacrylate.

In some embodiments of Composition (C), the at least one hydroxyl-containing monomer is a hydroxysilicone monomer. In certain embodiments, the hydroxysilicone monomer is selected from 3-(3-(1,1,1,3,5,5,5-heptamethyltrisiloxan-3-yl)propoxy)-2-hydroxypropyl methacrylate (SiMAA), mono-n-butyl terminated monomethacryloxypropyl terminated polydimethylsiloxane (mPDMS), and mono-(2-hydroxy-3-methacryloxypropyl)-propyl ether terminated mono-n-butyl terminated polydimethylsiloxane (OH-mPDMS).

In some embodiments, the reactive monomer mixture comprises the at least one hydroxyl-containing monomer in an amount between about 1 and about 20 weight percent, including about 1, 2, 3, 4, 5, 6, 7, 8, 9, 10, 11, 12, 13, 14, 15, 16, 17, 18, 19, and 20 weight percent. In certain embodiments, the reactive monomer mixture comprises the hydroxyl-containing monomer in an amount between about 5 and about 15 weight percent, including about 5, 6, 7, 8, 9, 10, 11, 12, 13, 14, and 15 weight percent. In some embodiments, the weight percent of the at least one hydroxyl-containing monomer present in the reactive monomer mixture is calculated excluding a diluent.

In some embodiments, Composition (C) further comprises at least one hydrophilic monomer. In certain embodiments, the at least one hydrophilic monomer is selected from vinyl pyrrolidone, N-vinyl -N-methyl acetamide, N-methyl methacrylamide, N-vinyl acetamide, N,N-dimethylacrylamide, hydroxyethyl acrylamide, N-(2-hydroxypropyl)acrylamide, N-(3-hydroxypropyl)acrylamide, poly(ethylene glycol) methyl ether methacrylate, poly(ethylene glycol) methacrylate, or any combination thereof.

In some embodiments of Composition (C), the at least one crosslinking agent is selected from the group consisting of a non-cycloaliphatic crosslinking agent, a cycloaliphatic crosslinking agent, and any combination thereof. In certain embodiments, the at least one crosslinking agent is a non-cycloaliphatic crosslinking agent selected from ethylene glycol di(meth)acrylate, diethylene glycol di(meth)acrylate, triethylene glycol di(meth)acrylate, tetraethylene glycol di(meth)acrylate, trimethylolpropane tri(meth)acrylate, glycerol tri(meth)acrylate, triallyl cyanurate, methylene bis (meth)acrylamide, poly(ethylene glycol) di(meth)acrylate, bis(2-hydropropyl (meth)acrylate) terminated polydimethylsiloxanes, and any combination thereof. In more certain embodiments, the non-cycloaliphatic crosslinking agent is ethylene glycol dimethacrylate. In particular embodiments, the at least one crosslinking agent is a cycloaliphatic crosslinking agent comprising cycloaliphatic groups having between one and four cycloaliphatic rings. In yet more particular embodiments, the cycloaliphatic crosslinking agent is tricyclo[5.2.1.0$^{2.6}$]decanedimethanol di(meth)acrylate.

In some embodiments, the reactive monomer mixture comprises the cycloaliphatic crosslinking agent in an amount between about 1 and about 20 weight percent, between about 3 and about 15 weight percent, or between about 3 and about 10 weight percent. In some embodiments, the weight percent of the cycloaliphatic crosslinking agent present in the reactive monomer mixture is calculated excluding a diluent.

In some embodiments of Composition (C), the at least one crosslinking agent has the formula:

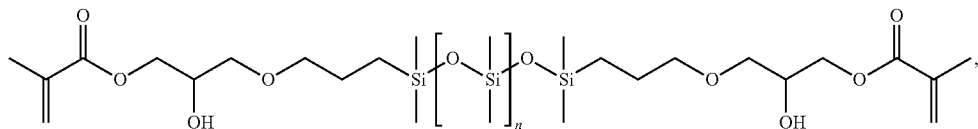

wherein n is an integer from 5 to 50, including 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50. In certain embodiments, n is an integer from 10 to 40. In certain embodiments, n is an integer from 15 to 30. In certain embodiments, n is an integer from 15 to 25. In certain embodiments, n is 15, 16, 17, 18, 19, 20, 21, 22, 23, 24, or 25. In yet more certain embodiments, n is 20.

In some embodiments, the reactive monomer mixture comprises the at least one crosslinking agent in an amount of about 15% to about 22% by weight, including about 15, 16, 17, 18, 19, 20, 21, and 22% by weight. In certain embodiments, the reactive monomer mixture comprises the at least one crosslinking agent in an amount of about 16% to about 20% by weight, including about 16, 17, 18, 19, and 20% by weight. In more certain embodiments, the reactive monomer mixture comprises the at least one crosslinking agent in an amount of about 18% by weight. In some embodiments, the % by weight of the at least one crosslinking agent present in the reactive monomer mixture is calculated excluding a diluent.

In some embodiments, the at least one polyamide is selected from poly(vinyl pyrrolidone), poly(N-vinyl-N-methyl acetamide), poly(N-vinyl acetamide), poly(dimethyl acrylamide), and a copolymer or a mixture thereof.

In some embodiments of Composition (C), the at least one polyamide is poly(vinyl pyrrolidone) or poly(N-vinyl-N-methyl acetamide). In certain embodiments, the polyamide is a copolymer.

In some embodiments, the reactive monomer mixture comprises the at least one polyamide in an amount between about 0.1 weight percent and about 3 weight percent, including about 0.1, 0.5, 1, 2, and 3 weight percent. In certain embodiments, the reactive monomer mixture comprises the at least one polyamide in an amount between about 0.25 weight percent and about 2 weight percent, including about 0.25, 0.5, 1, and 2 weight percent. In some embodiments, the weight percent of the at least one polyamide present in the reactive monomer mixture is calculated excluding a diluent.

In some embodiments, the Composition (C) is made by free radical polymerization of a reactive monomer mixture comprising: (a) at least one hydrophobic (meth)acrylate that is an aromatic (meth)acrylate selected from 2-phenylethyl (meth)acrylate, 2-phenoxyethyl (meth)acrylate, 3-phenylpropyl (meth)acrylate, 3-phenoxypropyl (meth)acrylate, 1,3-bis(phenylthio)-2-propyl (meth)acrylate, and any combination thereof; (b) at least one hydroxyl-containing monomer selected from 2-hydroxyethyl (meth)acrylate, 3-hydroxypropyl (meth)acrylate, 2-hydroxypropyl (meth)acrylate, 4-hydroxybutyl (meth)acrylate, and any combination thereof, (c) at least one bis(2-hydroxypropyl (meth)acrylate) terminated polysiloxane crosslinking agent having formula:

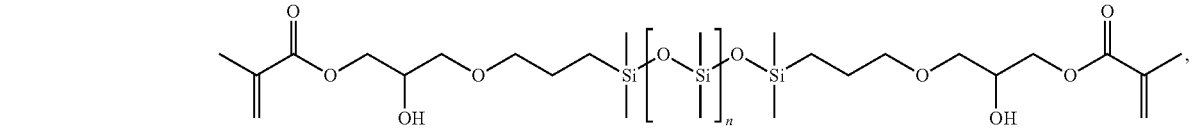

wherein n is an integer from 5 to 50 (e.g., 15 to 25); and (d) at least one polyamide selected from poly(vinyl pyrrolidone) and poly(N-vinyl-N-methyl acetamide), wherein the reactive monomer mixture comprises the at least one polyamide in an amount of about 0.10 to about 5.0 weight percent.

In some embodiments, Composition (C) further comprises at least one UV absorbing compound in the reactive monomer mixture. The UV absorbing compound may take the form of Formula I, above. In certain embodiments, the at least one UV absorbing compound is 2-(2'-hydroxy-5-methacrylyloxyethylphenyl)-2H-benzotriazole, 2-(2-cyano-2-(9H-thioxanthen-9-ylidene)acetamido)ethyl methacrylate, 2-(2-cyano-2-(9H-xanthen-9-ylidene)acetamido)ethyl methacrylate, 2-(2-cyano-2-(10-methylacridin-9(10H)-ylidene)acetamido)ethyl methacrylate, or any combination thereof. In certain embodiments, the at least one UV absorbing compound is 2-(2-cyano-2-(9H-thioxanthen-9-ylidene)acetamido)ethyl methacrylate.

In some embodiments, the reactive monomer mixture comprises the at least one UV absorbing compound in an amount between about 0.1 and about 5 weight percent, including about 0.1, 0.5, 1, 2, 3, 4, and 5 weight percent, between about 1 and about 4 weight percent, including about 1, 2, 3, and 4 weight percent, or between about 1 and about 3 weight percent, including 1, 2, and 3 weight percent. In some embodiments, the weight percent of the at least one UV absorbing compound present in the reactive monomer mixture is calculated excluding a diluent.

In some embodiments, Composition (C) further comprises at least one diluent in the reactive monomer mixture.

In some embodiments, Composition (C) has a water content of between about 0 weight percent and about 15 weight percent, including about 0, 0.1, 0.5, 1, 2, 3, 4, 5, 6, 7, 8, 9, 10, 11, 12, 13, 14, and 15 weight percent, between about 1 weight percent and about 10 weight percent, including about 1, 2, 3, 4, 5, 6, 7, 8, 9, and 10 weight percent, or between about 1 weight percent and about 8 weight percent, including about 1, 2, 3, 4, 5, 6, 7, and 8 weight percent.

In some embodiments of Composition (C), the composition has a refractive index of at least 1.45 and an Abbe number of at least 45; in other embodiments, the composition has a refractive index of at least 1.48 and an Abbe number of at least 50; or, in yet other embodiments, the composition has a refractive index of at least 1.50 and an Abbe number of at least 50.

In some embodiments of Composition (C), the free radical polymerization is a photopolymerization using a bisacylphosphine oxide initiator. In some embodiments, the initiator is bis(2,4,6-trimethylbenzoyl)-phenylphosphineoxide.

C. Ophthalmic Devices

In some embodiments, the presently disclosed subject matter provides a device comprising a Composition (A, B or C) as described immediately hereinabove.

In particular embodiments, the ophthalmic device comprises a lens, inlay, outlay, or insert selected from an intraocular implant or lens, a contact lens, a corneal inlay, a corneal outlay, and a corneal insert.

In specific embodiments, the ophthalmic device is an intraocular implant or lens. More specifically, the presently disclosed subject matter also provides intraocular implants and/or lenses made at least partially or completely from the compositions (A-C) described herein. Such intraocular implants or lenses can include an optic portion and one or more haptic portions. Typically, the compositions of the presently disclosed subject matter will make up part or all of the optic portion of the intraocular implant or lens. In some embodiments, the optic portion of the implant or lens will have a core made from one of the compositions described herein surrounded by different polymer or material. Implants or lenses in which the optic portion is made up of at least partially of one of the compositions of the presently disclosed subject matter will usually also have a haptic portion. The haptic portion can also be made of polymer of the disclosure or can be made of a different material, for example another polymer.

In some embodiments, the intraocular implant or lens of the presently disclosed subject matter is a one-piece lens having a soft, foldable central optic region and an outer peripheral region (haptic-region) in which both regions are made of the same polymer. In other embodiments, the optic and haptic regions can be formed from different types of polymers or materials, if desired. Some implants or lenses can also have haptic portions that are made up of different materials, for example where one or more haptic portions is made from the same material as the optic portion and other haptic portions are made of materials other than a polymer of the disclosure. Multicomponent implants or lenses can be made by embedding one material in the other, concurrent extrusion processes, solidifying the hard material about the soft material, or forming an interpenetrating network of the rigid component into a preformed hydrophobic core. In instances where one or more haptic portions are made from a different material than the optic portion of the lens, the haptic portion can be attached to the optic portion in any manner known in the art, such as by drilling a hole or holes in the optic portion and inserting the haptic portion.

The compositions described herein have been designed so that they are capable of being folded so that the intraocular lens can be inserted into the eye of an individual through a small incision. The haptic portion of the lens provides the required support for the implant or lens in the eye after insertion and unfolding of the lens and tends to help stabilize the position of the lens after insertion and the closure of the incision. The shape of the haptic portion design is not particularly limited and can be any desired configuration, for example, either a plate type or graduated thickness spiral filaments, also known as a C-loop design.

The optic portion of the intraocular lens can be approximately 2-6 mm in diameter prior to hydration. The 2-6 mm diameter is fairly standard in the art, and is generally chosen to cover the pupil in its fully dilated state under naturally occurring conditions. However, other sizes are contemplated and the presently disclosed subject matter is not limited to any particular diameter or size of intraocular lens. Furthermore, it is not necessary that the lens optic portion be circular; it could also be oval, square, or any other shape as desired.

The intraocular lens can further include one or more non-optical haptic components extending away from the outermost peripheral surface of the optic portion. The haptic components can be of any desired shape, for example, graduated spiral filaments or flat plate sections and are used to support the lens within the posterior chamber of the eye. Lenses having any desired design configuration can be fabricated. Should the intraocular lens include other components besides the optical and haptic portions, such other portions can be made of a polymer as are the haptic and optic portions, or if desired, another material.

The intraocular implants lenses may be inserted into the eye in any manner known in the art. For example, the intraocular lens may be folded prior to insertion into the eye using an intraocular lens inserter or by small, thin forceps of the type typically used by ophthalmic surgeons. After the implant or lens is in the targeted location, it is released to unfold. As is well known in the art, typically the lens that is to be replaced is removed prior to insertion of the intraocular lens. The intraocular lens of the presently disclosed subject matter can be made of a generally physiologically inert soft polymeric material that is capable of providing a clear, transparent, refractive lens body even after folding and unfolding. In some embodiments, the foldable intraocular lens of the presently disclosed subject matter can be inserted into any eye by injection whereby the mechanically compliant material is folded and forced through a small tube such as a 1 mm to 3 mm inner diameter tube.

D. Method for Making an Ophthalmic Device

In still yet other embodiments, the presently disclosed subject matter provides a method for making an ophthalmic device, the method comprising: (a) providing any one of Composition (A), Composition (B), or Composition (C); and (b) forming an ophthalmic device. In other embodiments, the presently disclosed subject matter provides a method for making an ophthalmic device, the method comprising: (a) preparing a blank from any one of Composition (A), Composition (B), or Composition (C); and (b) machining an ophthalmic device from the blank. In other embodiments, the presently disclosed subject matter provides a method for making an ophthalmic device, the method comprising molding a lens from any one of Composition (A), Composition (B), or Composition (C). In other embodiments, the presently disclosed subject matter provides a method for making an ophthalmic device, the method comprising molding a lens from any one of Composition (A), Composition (B), or Composition (C); and (b) machining the lens to refine the surface characteristics. In certain embodiments of either method, the method further comprises the step of extracting the ophthalmic device with a solvent. In certain embodiments, the method further comprises the step of hydrating the extracted ophthalmic device with at least one aqueous solution. In particular embodiments, the method further comprises an irradiation step using a laser, which in certain embodiments, is a two photon laser, which in more certain embodiments, is a femtosecond two photon laser. In more particular embodiments, the method further comprises a step of sterilizing the ophthalmic device. The ophthalmic device may be sterilized by known means such as, but not limited to, autoclaving.

Some embodiments of the disclosure will now be described in detail in the following Examples.

EXAMPLES

Refractive Index Test Method: Refractive index was measured using an Anton Paar Abbemat WR-wavelength refractometer. The instrument was equilibrated at 35° C. for a minimum of 1 hour prior to use. The measurement wavelength was set at 589.3 nanometers. Using a pair of tweezers, the sample was placed on the quartz plate. The instrument lid was closed, and the refractive index was recorded after 60 seconds of dwell time. Measurements were performed on three samples, and the average was reported.

Abbe Number Test Method: Following the steps for measuring the refractive index at 589.3 nm, the refractive index at 486.1 nm and 656.3 nm were determined. The Abbe number was calculated as follows:

$$V_D = \frac{n_D - 1}{n_F - n_C};$$

where $n_D$, $n_F$ and $n_C$ are the refractive indices of the material at the wavelengths of the Fraunhofer D-, F- and C- spectral lines (589.3 nm, 486.1 nm and 656.3 nm respectively).

The following abbreviations will be used throughout the Examples and have the following meanings:

TL03 lights: Phillips TLK 40 W/03 bulbs
RMM: reactive monomer mixture(s)
BC: back or base curve plastic mold
FC: front curve plastic mold
Zeonor: Zeonor which is a polycycloolefin thermoplastic polymer (Nippon Zeon Co Ltd)
RI (35): refractive index measured at 35° C.
Abbe #(35): Abbe number measured at 35° C.
PEMA: 2-phenylethyl methacrylate (Melrob, Parmon)
PEA: 2-phenylethyl acrylate [CAS 3530-36-7] (Melrob, Parmon)
BPTPA: 1,3-bis(phenylthio)-2-propyl acrylate (Bimax)
HEMA: 2-hydroxyethyl methacrylate (Bimax)
HBA: 4-hydroxybutyl acrylate [CAS 2478-10-6] (TCI or BASF)
mPEG950: polyethylene glycol methyl ether methacrylate [CAS 26915-72-0] (Aldrich, $M_n$=950 g/mol) which may be purified by crystallization from diethyl ether)
PEGDMA: poly(ethylene glycol) dimethacrylate, $M_n$=1000 daltons (Polysciences)
EGDMA: ethylene glycol dimethacrylate (Esstech)
mPDMS: mono-n-butyl terminated monomethacryloxypropyl terminated polydimethylsiloxane ($M_n$=500-1500 daltons) (Gelest)
SiMAA: 2-propenoic acid, 2-methyl-2-hydroxy-3-[3-[1,3,3,3-tetramethyl-1-[(trimethylsilyl)oxy]disiloxanyl]propoxy]propyl ester (Toray) or 3-(3-(1,1,1,3,5,5,5-heptamethyltrisiloxan-3-yl)propoxy)-2-hydroxypropyl methacrylate
tBu-SiMAA: 3-(3-(1,5-di-tert-butyl-1,1,3,5,5-pentamethyltrisiloxan-3-yl)propoxy)-2-hydroxypropyl methacrylate
LMW HO-mPDMS: mono-n-butyl terminated mono-(2-hydroxy-3-methacryloxypropyloxy)-propyl terminated polydimethylsiloxane (molecular weight=612 daltons, n=4) (Ortec or DSM-Polymer Technology Group)
HMW HO-mPDMS: mono-n-butyl terminated mono-(2-hydroxy-3-methacryloxypropyloxy)-propyl terminated polydimethylsiloxane ($M_n$=1400 daltons, n=15) (Ortec or DSM-Polymer Technology Group)
ac-PDMS: bis-3-acryloxy-2-hydroxypropyloxypropyl polydimethylsiloxane (Tegomer V-Si 2250 from Evonik)
XLMA: bis-3-methacryloxy-2-hydroxypropyloxypropyl polydimethylsiloxane ($M_n$=2000 daltons, n=20) (Adesis or Shin Etsu)
UVB: 3-(3-(tert-butyl)-5-(5-chloro-2H-benzo[d][1,2,3]triazol-2-yl)-4-hydroxyphenyl)propyl methacrylate or 2-Methylacrylic acid, 3-[3-tert-butyl-5-(5-chlorobenzotriazol-2-yl)-4-hydroxyphenyl]-propyl ester (Adesis)
Omnirad 819: bis(2,4,6-trimethylbenzoyl)-phenylphosphineoxide [CAS 162881-26-7] (IGM Resins)
PVP K90: poly(N-vinylpyrrolidone) [CAS 9003-39-8] (Ashland)
PVMA 570 kDa: polyvinylmethyacetamide. PVMA was prepared as follows:
380 mL (3.48 mol) of distilled N-vinyl-N-methyl acetamide and 187 mg (1.14 mmol) of azobisisobutyronitrile were added to a 3-neck round bottom flask fitted with reflux condenser, magnetic stirring bar and thermocouple and purged of oxygen gas for 2 hours by bubbling nitrogen gas through the reaction mixture. Then, the reaction mixture was heated at 75° C. for 24 hours during which time the reaction mixture solidified. The reaction product was quenched in air and isolated by work-up procedure 1 or work-up procedure 2. Work-up Procedure: The reaction product was dissolved in water and dialyzed extensively in dialysis membrane tubing (Spectra Pore MWCO 3500) and freeze dried (60% yield) (LABCONCO, Freezone™ Triad™ freeze dry system, Model #7400030). The molecular weight was determined by Size Exclusion Chromatography with Multi-Angle Light Scattering (SEC-MALS). The SEC-MALS setup employed aqueous acetonitrile solution as the mobile phase composed of 80% (v/v) 50 mM $Na_2SO_4$ and 20% (v/v) acetonitrile at a flow rate of 0.5 mL/min at 40° C. Two Tosoh Biosciences TSK-gel columns in series were used [SuperAW4000 and SuperAW5000] with an online Agilent 1200 UVNIS diode array detector, a Wyatt Optilab rEX interferometric refractometer, and a Wyatt mini-DAWN Treos multiangle laser scattering (MALS) detector (λ=658 nm). Absolute molecular weights and polydispersity data were calculated using the Wyatt ASTRA VI SEC/LS software package. About 40 milligrams of PVMA were dissolved in packing solution in a 10 mL volumetric flask. Packing Solution: 18.52 grams (300 mmol) of boric acid, 3.7 grams (9.7 mmol) of sodium borate decahydrate, and 28 grams (197 mmol) of sodium sulfate were dissolved in enough deionized water to fill a 2-liter volumetric flask. Three different solutions were prepared and tested. All solutions were filtered through a 0.45-micron nylon membrane filter prior to injection into the SEC-MALS system. The number average molecular weight of the three samples was 290.5 kDa; the weight average molecular weight of the three samples was 570.3 kDa; resulting in a polydispersity index of 1.96.

Examples 1-11

Under yellow lighting, the RMMs listed in Tables 1 and 2 were degassed by sparging with nitrogen gas for at least 3 minutes, and back filling the headspace in the container with nitrogen gas. The container was immediately transferred into a fill box having a nitrogen gas atmosphere with less than 0.1% (v/v) oxygen gas and an internal temperature at ambient temperature. About 75-100 μL of the reactive mixture were dosed using an Eppendorf pipet at room temperature into the FC made of Zeonor. The BC also made of Zeonor was then placed onto the FC. The FC and BC were designed to make disk samples having a thickness of about 85 microns. The molds were equilibrated for a minimum of twelve hours in the glove box prior to dosing. Pallets containing eight mold assemblies each were transferred into an adjacent glove box maintained between 55° C. and 60° C., and the lenses were cured from the top using TL03 lights having an intensity of 3.5-4.0 mW/cm$^2$ at the tray's location for 15 minutes. The cured assemblies were manually demolded. Examples 1, 3-5, and 9-11 were transparent and exhibited no surface tackiness; examples 2, 5, and 10 were hazy. Examples 2, 6, and 7-8 were stiff. Examples 1, 3, 4, 6-9, and 11 exhibited good shape memory when folded and allowed to relax back into the original shape. For each example, the refractive index and Abbe numbers were determined and listed in Tables 1 and 2. Samples were subsequently hydrated by submerging in deionized water and allowed to equilibrate at 37° C. for a minimum of 48 hours. Samples were briefly blotted with blotting paper to remove excess surface water; weighed; placed in an oven at 109° C. for 24 hours; reweighed; and then, the percent water content calculated using the following formula: [(hydrated weight-dry weight)/hydrated weight]×100%. Refractive index and Abbe numbers were determined with an Anton Paar Abbemat WR Multi-wavelength refractometer (Part Number 89608). For hydrated polymers, the samples were briefly blotted using blotting paper to remove excess surface water, prior to measurements.

TABLE 1

|  | Ex. 1 | Ex. 2 | Ex. 3 | Ex. 4 | Ex. 5 | Ex. 6 |
|---|---|---|---|---|---|---|
| Components (weight %) | | | | | | |
| PEA | 50 | 50 | | | | |
| PEMA | 30 | 30 | 35 | 33.32 | 33.32 | 74.65 |
| BPTPA | | | 35 | 33.33 | 33.33 | |
| HEMA | | 14.65 | 10 | 10 | | |
| HBA | 14.65 | | | | 10 | 20 |
| mPEG950 | | | | 18 | 18 | |
| PVP K90 | | | 1.75 | 1.75 | 1.75 | |
| PVMA | 1.75 | 1.75 | | | | 1.75 |
| EGDMA | 3.5 | 3.5 | | 3.5 | 3.5 | 3.5 |
| PEGDMA | | | 18.15 | | | |
| Omnirad 819 | 0.1 | 0.1 | 0.1 | 0.1 | 0.1 | 0.1 |
| Properties | | | | | | |
| RI (35) | 1.535046 (0.000535) | 1.540583 | 1.542245 (0.001845) | 1.512779 (0.000288) | 1.518754 (0.002510) | 1.535018 (0.000764) |
| Abbe # (35) | 43 (1) | 40 | 44 (5) | 39 (0) | 41 (2) | 41 (1) |
| Appearance | Transparent | Hazy | Transparent | Transparent | Hazy | Transparent |
| Shape Memory | Good | Stiff | Good | Good | Good | Stiff |
| Water Content (weight %) | 3.9 | 3.7 | 10.1 | 18.4 | 17.7 | 5.5 |

TABLE 2

| Components (weight %) | Ex. 7 | Ex. 8 | Ex. 9 | Ex. 10 | Ex. 11 |
|---|---|---|---|---|---|
| PEA | | | 35 | 35 | 35 |
| PEMA | 69.1 | 68 | 35 | 35 | 35 |
| HEMA | 9.6 | | 10 | 10 | |
| HBA | | 12 | | | 10 |
| PVP K90 | | | 1.75 | | |
| PVMA | 1.9 | 1.75 | | 1.75 | 1.75 |
| XLMA (Adesis) | 19.25 | 17.15 | 18.15 | 18.15 | 18.15 |
| Omnirad 819 | 0.1 | 0.1 | 0.1 | 0.1 | 0.1 |

TABLE 2-continued

| Properties | Ex. 7 | Ex. 8 | Ex. 9 | Ex. 10 | Ex. 11 |
|---|---|---|---|---|---|
| RI (35) | 1.522608 (0.001596) | 1.512790 (0.000620) | 1.518375 (0.001449) | 1.508399 (0.008893) | 1.514937 (0.001415) |
| Abbe # (35) | 52 (2) | 46 (1) | 49 (2) | 48 (2) | 48 (1') |
| Appearance | Transparent | Transparent | Transparent | Hazy | Transparent |
| Shape Memory | Stiff | Stiff | Good | Good | Good |
| Water Content (weight %) | 11.8 | 4.5 | 3.4 | 6.7 | 5.3 |

The RMM shown in Table 1 and Table 2 all include at least one aromatic (meth)acrylate monomer, at least one hydroxyalkyl (meth)acrylate monomer and a wetting agent (PVP or PVMA). The key variable between these examples is the crosslinker. The materials in Table 1, which use EGDMA or PEGDMA as a crosslinker, have Abbe numbers ranging from 39-44. In contrast the materials shown in Table 2, which use XLMA as a crosslinker, have higher Abbe numbers ranging from 46-52.

Examples 12-16

Under yellow lighting, the RMMs listed in Table 3 was degassed by sparging with nitrogen gas for at least 3 minutes, and back filling the headspace of the container with nitrogen gas. and the container was then immediately transferred into a fill box having a nitrogen gas atmosphere with less than 0.1% (v/v) oxygen gas and an internal temperature at ambient temperature. About 75-100 μL of the reactive mixture were dosed using an Eppendorf pipet at room temperature into the FC made of Zeonor. The BC also made of Zeonor was then placed onto the FC. The FC and BC were designed to make disk samples having a thickness of about 85 microns. The molds were equilibrated for a minimum of twelve hours in the glove box prior to dosing. Pallets containing eight mold assemblies each were transferred into an adjacent glove box maintained between 55° C. and 60° C., and the lenses were cured from the top using TL03 lights having an intensity of 5-6 mW/cm$^2$ at the tray's location for 25 minutes. The cured assemblies were manually demolded. Examples 12, 14, 15, and 16 were transparent and exhibited no surface tackiness. Examples 13 was slightly hazy but became transparent when hydrated. Examples 12-16 exhibited good shape memory when folded and allowed to relax back into the original shape. For each example, the refractive index and Abbe numbers were determined and listed in Table 3.

TABLE 3

| Components (weight %) | Ex. 12 | Ex. 13 | Ex. 14 | Ex. 15 | Ex. 16 |
|---|---|---|---|---|---|
| PEA | 35 | 35 | 34.5 | 34.5 | 34.5 |
| PEMA | 35 | 35 | 34.5 | 34.5 | 34.5 |
| HEMA | 10 | 9.96 | 9.36 | 9.36 | 9.36 |
| PVP K90 | 1.75 | 1.75 | 1 | 1 | 1 |
| XLMA (Adesis) | 18.15 | | | | |
| XLMA (Shin Etsu) | | 18.15 | | | |
| EGDMA | | | 2.5 | 2.5 | 2.5 |
| OH-mPDMS n = 4 | | | 18 | | |
| OH-mPDMS n = 15 | | | | 18 | |
| tBu-SiMAA | | | | | 18 |
| Omnirad 819 | 0.1 | 0.14 | 0.14 | 0.14 | 0.14 |
| Properties | Ex.12 | Ex. 13 | Ex. 14 | Ex. 15 | Ex. 16 |
| RI (35) | 1.519583 (0.000867) | 1.515621 (0.000784) | 1.524109 (0.000199) | 1.520478 (0.000373) | 1.526413 (0.000631) |
| Abbe # (35) | 51 (2) | 47 (2) | 44 (0) | 43 (0) | 44 (0) |
| Appearance | Transparent | Hazy | Transparent | Transparent | Transparent |
| Shape Memory | Good | Good | Good | Good | Good |

The RMM shown in Table 3 all include at least one aromatic (meth)acrylate monomer, at least one hydroxyalkyl (meth) acrylate monomer, a wetting agent and a hydroxysilicone component. These examples again demonstrate that selection of crosslinker has an impact Abbe number, with the XLMA crosslinker producing higher Abbe numbers.

CLAUSES

For reasons of completeness, various aspects of the disclosure are set forth in the following numbered clauses.

Clause 1. A composition made by free radical polymerization of a reactive monomer mixture comprising:
  a. at least one aromatic (meth)acrylate;
  b. at least one hydroxyalkyl (meth)acrylate;
  c. at least one polyamide; and
  d. at least one bis(2-hydroxypropyl (meth)acrylate) terminated polysiloxane crosslinking agent;
  wherein the composition exhibits a refractive index of at least 1.45 and an Abbe number of at least 39.

Clause 2. The composition of clause 1, wherein the aromatic (meth)acrylate is selected from 2-phenylethyl (meth)acrylate, 2-phenoxyethyl (meth)acrylate, 3-phenylpropyl (meth)acrylate, 3-phenoxypropyl (meth)acrylate, 1,3-bis-(phenylthio)-2-propyl (meth)acrylate, poly(ethylene glycol) phenyl ether (meth)acrylate, and any combination thereof.

Clause 3. The composition of clause 1 or clause 2, wherein the hydroxyalkyl (meth)acrylate comprises a linear, branched, or cyclic hydroxyalkyl group having between one and twenty-five carbon atoms.

Clause 4. The composition of clause 3, wherein the hydroxyalkyl (meth)acrylate is selected from 2-hydroxyethyl (meth)acrylate, 3-hydroxypropyl (meth)acrylate, 2-hydroxypropyl (meth)acrylate, 4-hydroxybutyl (meth)acrylate, and any combination thereof.

Clause 5. The composition of any one of clauses 1-4, wherein the polyamide is selected from poly(vinyl pyrrolidone), poly(N-vinyl-N-methyl acetamide), poly(N-vinyl acetamide), poly(dimethyl acrylamide), and a copolymer or a mixture thereof.

Clause 6. The composition of clause 5, wherein the polyamide is selected from poly(vinyl pyrrolidone) and poly(N-vinyl-N-methyl acetamide).

Clause 7. The composition of clause 5, wherein the polyamide is a copolymer.

Clause 8. The composition of any one of clauses 1-7, wherein the reactive monomer mixture comprises the polyamide in an amount between about 0.1 weight percent and about 5 weight percent, between about 0.5 weight percent and about 3 weight percent, or between about 0.5 weight percent and about 2 weight percent.

Clause 9. The composition of any one of clauses 1-8, wherein the crosslinking agent is selected from a bis(2-hydroxypropyl (meth)acrylate) terminated poly(dialkylsiloxane), a bis(2-hydroxypropyl (meth)acrylate) terminated poly(diarylsiloxane), a bis(2-hydropropyl (meth)acrylate) terminated poly(dialkyl-co-diarylsiloxane), or any combination thereof, wherein the alkyl group in each instance is a linear, branched or cyclic hydrocarbon group containing between one and twenty-five carbon atoms, and the aryl group in each instance is benzyl, phenyl, or substituted phenyl.

Clause 10. The composition of clause 9, wherein the crosslinking agent is a bis(2-hydroxypropyl (meth)acrylate) terminated poly(dimethylsiloxane).

Clause 11. The composition of clause 10, wherein the reactive monomer mixture comprises the bis(2-hydroxypropyl (meth)acrylate) terminated poly(dimethylsiloxane) in an amount between about 15 weight percent and 30 weight percent.

Clause 12. The composition of any one of clauses 1-11, further comprising at least one hydrophilic monomer.

Clause 13. The composition of clause 12, wherein the hydrophilic monomer is selected from vinyl pyrrolidone, N-vinyl-N-methyl acetamide, N-methyl methacrylamide, N-vinyl acetamide, N,N-dimethylacrylamide, or any combination thereof.

Clause 14. The composition of any one of clauses 1-13, further comprising at least one hydroxy silicone monomer.

Clause 15. The composition of clause 14, wherein the hydroxy silicone monomer comprises mono-n-butyl terminated mono-(2-hydroxy-3-methacryloxypropyloxy)-propyl terminated polydimethylsiloxane, 3-(3-(1,1,1,3,5,5,5-heptamethyltrisiloxan-3-yl)propoxy)-2-hydroxypropyl methacrylate, 3-(3-(1,5-di-tert-butyl-1,1,3,5,5-pentamethyltrisiloxan-3-yl)propoxy)-2-hydroxypropyl methacrylate, or any combination thereof.

Clause 16. The composition of any one of clauses 1-15, further comprising at least one UV absorbing compound in the reactive monomer mixture.

Clause 17. The composition of clause 16, wherein the UV absorbing compound comprises a compound in the form of Formula I, 2-(2'-hydroxy-5-methacrylyloxyethylphenyl)-2H-benzotriazole, 2-(2-cyano-2-(9H-thioxanthen-9-ylidene)acetamido)ethyl methacrylate, 2-(2-cyano-2-(9H-xanthen-9-ylidene)acetamido)ethyl methacrylate, 2-(2-cyano-2-(10-methylacridin-9(10H)-ylidene)acetamido)ethyl methacrylate or any combinations thereof.

Clause 18. The composition of clause 16 or clause 17, wherein the reactive monomer mixture comprises the UV absorbing compound in an amount between about 0.1 and about 5 weight percent, between about 1 and about 4 weight percent, or between about 1 and about 3 weight percent.

Clause 19. The composition of any one of clauses 1-18, further comprising an unsaturated monomer having a polymerizable group and at least one other carbon-carbon double bond.

Clause 20. The composition of clause 19, wherein the polymerizable group comprises a (meth)acrylate, a styrene, a vinyl ether, a (meth)acrylamide, an N-vinyllactam, an N-vinylamide, an O-vinylcarbamate, an O-vinylcarbonate, a vinyl group, or any combination thereof.

Clause 21. The composition of clause 19 or clause 20, wherein the carbon-carbon double bond is present in a linear, branched or cyclic aliphatic hydrocarbon moiety having between two and thirty carbon atoms.

Clause 22. The composition any one of clauses 19-21, wherein the unsaturated monomer is selected from cyclohexenyl ether acrylate, N,N-diallyl acrylamide, diallyl maleate, allyl (meth)acrylate, 2-(allyloxy)ethyl (meth)acrylate, ((1R,2S,4R)-bicyclo[2.2.1]hept-5-en-2-yl)methyl (meth)acrylate, ethylene glycol dicyclopentenyl ether (meth)acrylate, and any combination thereof.

Clause 23. The composition of any one of clauses 1-22, further comprising at least one diluent in the reactive monomer mixture.

Clause 24. The composition of any one of clauses 1-23, having a water content of between about 0 weight percent and 15 weight percent, between about 0.5 weight percent and about 10 weight percent, or between about 1 weight percent and about 8 weight percent.

Clause 25. The composition of any one of clauses 1-24, wherein the composition has a refractive index of at least 1.45 and an Abbe number of at least 45; wherein the composition has a refractive index of at least 1.48 and an Abbe number of at least 50; or wherein the composition has a refractive index of at least 1.50 and an Abbe number of at least 50.

Clause 26. The composition of any one of clauses 1-25, wherein the free radical polymerization is a photopolymerization using a bisacylphosphine oxide initiator.

Clause 27. An ophthalmic device comprising the composition of any one of clauses 1-26.

Clause 28. The ophthalmic device of clause 27, wherein the ophthalmic device comprises an intraocular lens, contact lens, corneal inlay, corneal outlay, or corneal insert.

Clause 29. A method for making an ophthalmic device, the method comprising:
  a. providing a composition of any one of clauses 1-26; and
  b. forming an ophthalmic device.

Clause 30. The method of clause 29, further comprising the step of extracting the ophthalmic device with a solvent.

Clause 31. The method of clause 30, further comprising the step of hydrating the extracted ophthalmic device with at least one aqueous solution.

Clause 32. A method for making an ophthalmic device, the method comprising either:
  a. preparing a blank from the composition of any of clauses 1-26 and machining an ophthalmic device from the blank;
  b. molding an ophthalmic device from the composition of any of clauses 1-26; or
  c. molding an ophthalmic device from the composition of any of clauses 1-26 and machining the surface of the ophthalmic device.

Clause 33. The method of clause 32, further comprising the step of extracting the ophthalmic device with a solvent.

Clause 34. The method of clause 33, further comprising the step of hydrating the extracted ophthalmic device with at least one aqueous solution.

Clause 35. The method of any one of clauses 29-34, further comprising an irradiation step using a femtosecond two photon laser.

Clause 36. The method of any of clauses 29-35, further comprising a step of sterilizing the ophthalmic device.

Clause 37. A composition made by free radical polymerization of a reactive monomer mixture comprising:
  a. at least one aromatic (meth)acrylate;
  b. at least one hydroxyalkyl (meth)acrylate; and
  c. at least one bis(2-hydroxypropyl (meth)acrylate) terminated polysiloxane crosslinking agent:
  wherein the crosslinking agent is present in the reactive monomer mixture in an amount of about 15% to about 22% by weight.

Clause 38. The composition of clause 37, wherein the aromatic (meth)acrylate is selected from 2-phenylethyl (meth)acrylate, 2-phenoxyethyl (meth)acrylate, 4-chlorophenoxyethyl (meth)acrylate, 3-phenylpropyl (meth)acrylate, 3-phenoxypropyl (meth)acrylate, 1,3-bis-(phenylthio)-2-propyl (meth)acrylate, poly(ethylene glycol) phenyl ether (meth)acrylate, and any combination thereof.

Clause 39. The composition of clause 37 or clause 38, wherein the aromatic (meth)acrylate is 2-phenylethyl acrylate.

Clause 40. The composition of clause 37 or clause 38, wherein the aromatic (meth)acrylate is 2-phenylethyl methacrylate.

Clause 41. The composition of clause 37 or clause 38, wherein the aromatic (meth)acrylate is a combination of 2-phenylethyl acrylate and 2-phenylethyl methacrylate.

Clause 42. The composition of any one of clauses 37-41, wherein the reactive monomer mixture comprises the aromatic (meth)acrylate in an amount between about 40 and about 80 weight percent.

Clause 43. The composition of any one of clauses 37-42, wherein the reactive monomer mixture comprises the aromatic (meth)acrylate in an amount between about 60 and about 75 weight percent.

Clause 44. The composition of any one of clauses 37-43, wherein the hydroxyalkyl (meth)acrylate is selected from 2-hydroxyethyl (meth)acrylate, 2-hydroxypropyl (meth)acrylate, 3-hydroxypropyl (meth)acrylate, 4-hydroxybutyl (meth)acrylate, and any combination thereof.

Clause 45. The composition of clause 44, wherein the hydroxyalkyl (meth)acrylate is 2-hydroxyethyl methacrylate or 4-hydroxybutyl acrylate.

Clause 46. The composition of any one of clauses 37-45, wherein the reactive monomer mixture comprises the hydroxyalkyl (meth)acrylate in an amount between about 1 and about 20 weight percent.

Clause 47. The composition of any one of clauses 37-46, wherein the reactive monomer mixture comprises the hydroxyalkyl (meth)acrylate in an amount between about 5 and about 15 weight percent.

Clause 48. The composition of any one of clauses 37-47, wherein the crosslinking agent is selected from a bis(2-hydroxypropyl (meth)acrylate) terminated poly(dialkylsiloxane), a bis(2-hydroxypropyl (meth)acrylate) terminated poly(diarylsiloxane), a bis(2-hydropropyl (meth)acrylate) terminated poly(dialkyl-co-diarylsiloxane), or any combination thereof, wherein the alkyl group in each instance is a linear, branched or cyclic hydrocarbon group containing between one and twenty five carbon atoms, and the aryl group in each instance is benzyl, phenyl, or substituted phenyl.

Clause 49. The composition of clause 48, wherein the crosslinking agent is a bis(2-hydroxypropyl (meth)acrylate) terminated poly(dimethylsiloxane).

Clause 50. The composition of any one of clauses 37-47, wherein the crosslinking agent has formula:

wherein n is an integer from 5 to 50.

Clause 51. The composition of clause 50, wherein n is 15, 16, 17, 18, 19, 20, 21, 22, 23, 24, or 25.

Clause 52. The composition of clause 51, wherein n is 20.

Clause 53. The composition of any one of clauses 37-52, wherein the reactive monomer mixture comprises the cross-linking agent in an amount of about 15% to about 22% by weight.

Clause 54. The composition of any one of clauses 37-53, wherein the reactive monomer mixture comprises the cross-linking agent in an amount of about 16% to about 20% by weight.

Clause 55. The composition of any one of clauses 37-54, wherein the reactive monomer mixture comprises the cross-linking agent in an amount of about 18% by weight.

Clause 56. The composition of any one of clauses 37-55, further comprising a polyamide.

Clause 57. The composition of clause 56, wherein the polyamide is selected from poly(vinyl pyrrolidone), poly(N-vinyl-N-methyl acetamide), poly(N-vinyl acetamide), poly(dimethyl acrylamide), and a copolymer or a mixture thereof.

Clause 58. The composition of clause 57, wherein the polyamide is poly(N-vinyl-N-methyl acetamide).

Clause 59. The composition of clause 57, wherein the polyamide is a copolymer.

Clause 60. The composition of any one of clauses 56-59, wherein the reactive monomer mixture comprises the polyamide in an amount between about 0.1 weight percent and about 5 weight percent, between about 0.5 weight percent and about 3 weight percent, or between about 0.5 weight percent and about 2 weight percent.

Clause 61. The composition of any one of clauses 37-60, further comprising at least one UV absorbing compound in the reactive monomer mixture.

Clause 62. The composition of clause 61, wherein the UV absorbing compound is a compound of Formula I, 2-(2'-hydroxy-5-methacrylyloxyethylphenyl)-2H-benzotriazole, 2-(2-cyano-2-(9H-thioxanthen-9-ylidene)acetamido)ethyl methacrylate, 2-(2-cyano-2-(9H-xanthen-9-ylidene)acetamido)ethyl methacrylate, 2-(2-cyano-2-(10-methylacridin-9(10H)-ylidene)acetamido)ethyl methacrylate, or any combination thereof.

Clause 63. The composition of clause 61 or clause 62, wherein the reactive monomer mixture comprises the UV absorbing compound in an amount between about 0.1 and about 5 weight percent, between about 1 and about 4 weight percent, or between about 1 and about 3 weight percent.

Clause 64. The composition of any one of clauses 37-63, further comprising at least one diluent in the reactive monomer mixture.

Clause 65. The composition of any one of clauses 37-64, having a water content of between about 0 weight percent and about 15 weight percent, between about 1 weight percent and about 10 weight percent, or between about 1 weight percent and about 8 weight percent.

Clause 66. The composition of any one of clauses 37-65, wherein the composition has a refractive index of at least 1.45 and an Abbe number of at least 45; wherein the composition has a refractive index of at least 1.48 and an Abbe number of at least 50; or wherein the composition has a refractive index of at least 1.50 and an Abbe number of at least 50.

Clause 67. The composition of any one of clauses 37-66, wherein the free radical polymerization is a photopolymerization using a bisacylphosphine oxide initiator.

Clause 68. An ophthalmic device comprising the composition of any one of clauses 37-67.

Clause 69. The ophthalmic device of clause 68, wherein the ophthalmic device comprises an intraocular lens, contact lens, corneal inlay, corneal outlay, or corneal insert.

Clause 70. A method for making an ophthalmic device, the method comprising:
a. providing a composition of any one of clauses 37-67; and
b. forming an ophthalmic device.

Clause 71. The method of clause 70, further comprising the step of extracting the ophthalmic device with a solvent.

Clause 72. The method of clause 71, further comprising the step of hydrating the extracted ophthalmic device with at least one aqueous solution.

Clause 73. A method for making an ophthalmic device, the method comprising:
a. preparing a blank from the composition any of clauses 37-67;
b. machining an ophthalmic device from the blank.

Clause 74. The method of clause 73, further comprising the step of extracting the ophthalmic device with a solvent.

Clause 75. The method of clause 74, further comprising the step of hydrating the extracted ophthalmic device with at least one aqueous solution.

Clause 76. The method of any one of clauses 70-75, further comprising an irradiation step using a femtosecond two photon laser.

Clause 77. The method of any of clauses 70-76, further comprising a step of sterilizing the ophthalmic device.

Clause 78. A composition made by free radical polymerization of a reactive monomer mixture comprising:
a. at least one hydrophobic monomer;
b. at least one hydroxyl-containing monomer;
c. at least one crosslinking agent; and
d. at least one polyamide,
wherein the reactive monomer mixture comprises the polyamide in an amount of about 0.10 to about 5.0 weight percent.

Clause 79. The composition of clause 78, wherein the hydrophobic monomer is a hydrophobic (meth)acrylate monomer.

Clause 80. The composition of clause 78, wherein the hydrophobic (meth)acrylate is selected from an aliphatic (meth)acrylate, an aromatic (meth)acrylate, a cycloaliphatic (meth)acrylate, and any combination thereof.

Clause 81. The composition of clause 80, wherein the hydrophobic (meth)acrylate is an aliphatic (meth)acrylate.

Clause 82. The composition of clause 81, wherein the aliphatic (meth)acrylate is a $C_1$-$C_{18}$ alkyl (meth)acrylate.

Clause 83. The composition of clause 82, wherein the $C_1$-$C_{18}$ alkyl (meth)acrylate is selected from the group consisting of ethyl (meth)acrylate, n-butyl (meth)acrylate, iso-butyl (meth)acrylate, t-butyl (meth)acrylate, n-hexyl (meth)acrylate, 2-ethylhexyl (meth)acrylate, octyl (meth)acrylate, iso-decyl (meth)acrylate, heptadecyl (meth)acrylate, dodecyl (meth)acrylate, 2-propylheptyl (meth)acrylate, stearyl (meth)acrylate, and any combination thereof.

Clause 84. The composition of clause 83, wherein the $C_1$-$C_{18}$ alkyl (meth)acrylate is n-hexyl acrylate.

Clause 85. The composition of clause 80, wherein the hydrophobic (meth)acrylate is an aromatic (meth)acrylate.

Clause 86. The composition of clause 85, wherein the aromatic (meth)acrylate is selected from the group consisting of 2-phenylethyl (meth)acrylate, 2-phenoxyethyl (meth)acrylate, 4-chlorophenoxyethyl (meth)acrylate, 3-phenylpropyl (meth)acrylate, 3-phenoxypropyl (meth)acrylate, 1,3-bis-(phenylthio)-2-propyl (meth)acrylate, poly(ethylene glycol) phenyl ether (meth)acrylate, and any combination thereof.

Clause 87. The composition of clause 86, wherein the aromatic (meth)acrylate is 2-phenylethyl acrylate.

Clause 88. The composition of clause 86, wherein the aromatic (meth)acrylate is 2-phenylethyl methacrylate.

Clause 89. The composition of clause 86, wherein the aromatic (meth)acrylate is a combination of 2-phenylethyl acrylate and 2-phenylethyl methacrylate.

Clause 90. The composition of clause 80, wherein the hydrophobic (meth)acrylate is a cycloaliphatic (meth)acrylate.

Clause 91. The composition of clause 90, wherein the cycloaliphatic (meth)acrylate comprises cyclohexyl (meth)acrylate, cyclopentyl (meth)acrylate, 2-cyclohexylethyl (meth)acrylate, 3-cyclohexylpropyl (meth)acrylate, norbornyl (meth)acrylate, isobornyl (meth)acrylate, ((1R,2S,4R)-bicyclo[2.2.1]hept-5-en-2-yl)methyl (meth)acrylate, ethylene glycol dicyclopentenyl ether (meth)acrylate, or any combination thereof.

Clause 92. The composition of clause 91, wherein the cycloaliphatic (meth)acrylate is cyclohexyl acrylate.

Clause 93. The composition of clause 80, wherein the composition comprises an aliphatic (meth)acrylate, an aromatic (meth)acrylate, and a cycloaliphatic (meth)acrylate.

Clause 94. The composition of clause 93, wherein composition comprises cyclohexyl acrylate, phenylethyl acrylate, and n-hexyl acrylate.

Clause 95. The composition of any one of clauses 78-94, wherein the reactive monomer mixture comprises the hydrophobic monomer in an amount between about 50 and 90 weight percent.

Clause 96. The composition of any one of clauses 78-95, wherein the hydroxyl-containing monomer is a hydroxyalkyl (meth)acrylate.

Clause 97. The composition of clause 96, wherein the hydroxyalkyl (meth)acrylate comprises 2-hydroxyethyl (meth)acrylate, 2-hydroxypropyl (meth)acrylate, 3-hydroxypropyl (meth)acrylate, 4-hydroxybutyl (meth)acrylate, or any combination thereof.

Clause 98. The composition of clause 97, wherein the hydroxyalkyl (meth)acrylate is 2-hydroxyethyl methacrylate or 4-hydroxybutyl acrylate.

Clause 99. The composition of any one of clauses 78-95, wherein the hydroxyl-containing monomer is a hydroxysilicone monomer.

Clause 100. The composition of clause 99, wherein the hydroxysilicone monomer is selected from 3-(3-(1,1,1,3,5,5,5-heptamethyltrisiloxan-3-yl)propoxy)-2-hydroxypropyl methacrylate (SiMAA), mono-n-butyl terminated monomethacryloxypropyl terminated polydimethylsiloxane (mPDMS), and mono-(2-hydroxy-3-methacryloxypropyl)-propyl ether terminated mono-n-butyl terminated polydimethylsiloxane (OH-mPDMS).

Clause 101. The composition of any one of clauses 78-100, wherein the reactive monomer mixture comprises the hydroxyl-containing monomer in an amount between about 1 and about 20 weight percent.

Clause 102. The composition of clause 101, wherein the reactive monomer mixture comprises the hydroxyl-containing monomer in an amount between about 5 and about 15 weight percent.

Clause 103. The composition of any one of clauses 78-102, wherein the crosslinking agent is selected from the group consisting of a non-cycloaliphatic crosslinking agent, a cycloaliphatic crosslinking agent, and any combination thereof.

Clause 104. The composition of clause 103, wherein the crosslinking agent is a non-cycloaliphatic crosslinking agent selected from ethylene glycol di(meth)acrylate, diethylene glycol di(meth)acrylate, triethylene glycol di(meth)acrylate, tetraethylene glycol di(meth)acrylate, trimethylolpropane tri(meth)acrylate, glycerol tri(meth)acrylate, triallyl cyanurate, methylene bis(meth)acrylamide, poly(ethylene glycol) di(meth)acrylate, bis(2-hydropropyl (meth)acrylate) terminated polydimethylsiloxanes, and any combination thereof.

Clause 105. The composition of clause 104, wherein the non-cycloaliphatic crosslinking agent is ethylene glycol dimethacrylate.

Clause 106. The composition of clause 103, wherein the crosslinking agent is a cycloaliphatic crosslinking agent comprising cycloaliphatic groups having between one and four cycloaliphatic rings.

Clause 107. The composition of clause 106, wherein the cycloaliphatic crosslinking agent is tricyclo[5.2.1.0$^{2.6}$]decanedimethanol di(meth)acrylate.

Clause 108. The composition of clause 106 or clause 107, wherein the reactive monomer mixture comprises the cycloaliphatic crosslinking agent in an amount between about 1 and about 20 weight percent, between about 3 and about 15 weight percent, or between about 3 and about 10 weight percent.

Clause 109. The composition of any one of clauses 78-102, wherein the crosslinking agent has the formula:

wherein n is an integer from 5 to 50.

Clause 110. The composition of clause 109, wherein n is 15, 16, 17, 18, 19, 20, 21, 22, 23, 24, or 25.

Clause 111. The composition of clause 110, wherein n is 20.

Clause 112. The composition of any one of clauses 109-111, wherein the reactive monomer mixture comprises the crosslinking agent in an amount of about 15% to about 22% by weight.

Clause 113. The composition of any one of clauses 109-112, wherein the reactive monomer mixture comprises the crosslinking agent in an amount of about 16% to about 20% by weight.

Clause 114. The composition of any one of clauses 109-113, wherein the reactive monomer mixture comprises the crosslinking agent is present in the reactive monomer mixture in an amount of about 18% by weight.

Clause 115. The composition of any one of clauses 78-114, wherein the polyamide is selected from poly(vinyl pyrrolidone), poly(N-vinyl-N-methyl acetamide), poly(N-vinyl acetamide), poly(dimethyl acrylamide), and a copolymer or a mixture thereof.

Clause 116. The composition of clause 115, wherein the polyamide is poly(vinyl pyrrolidone) or poly(N-vinyl-N-methyl acetamide).

Clause 117. The composition of clause 115, wherein the polyamide is a copolymer.

Clause 118. The composition of any one of clauses 78-117, wherein the reactive monomer mixture comprises the polyamide in an amount between about 0.1 weight percent and about 3 weight percent.

Clause 119. The composition of any one of clauses 78-41, wherein the reactive monomer mixture comprises the polyamide in an amount between about 0.25 weight percent and about 2 weight percent.

Clause 120. The composition of any one of clauses 78-119, further comprising at least one UV absorbing compound in the reactive monomer mixture.

Clause 121. The composition of clause 120, wherein the UV absorbing compound is a compound of Formula I, 2-(2'-hydroxy-5-methacrylyloxyethylphenyl)-2H-benzotriazole, 2-(2-cyano-2-(9H-thioxanthen-9-ylidene)acetamido) ethyl methacrylate, 2-(2-cyano-2-(9H-xanthen-9-ylidene)acetamido)ethyl methacrylate, 2-(2-cyano-2-(10-methylacridin-9(10H)-ylidene)acetamido)ethyl methacrylate, or any combination thereof.

Clause 122. The composition of clause 120 or clause 121, wherein the reactive monomer mixture comprises the UV absorbing compound in an amount between about 0.1 and about 5 weight percent, between about 1 and about 4 weight percent, or between about 1 and about 3 weight percent.

Clause 123. The composition of any one of clauses 78-122, further comprising at least one diluent in the reactive monomer mixture.

Clause 124. The composition of any one of clauses 78-123, having a water content of between about 0 weight percent and about 15 weight percent, between about 1 weight percent and about 10 weight percent, or between about 1 weight percent and about 8 weight percent.

Clause 125. The composition of any one of clauses 78-124, wherein the composition has a refractive index of at least 1.45 and an Abbe number of at least 45; wherein the composition has a refractive index of at least 1.48 and an Abbe number of at least 50; or wherein the composition has a refractive index of at least 1.50 and an Abbe number of at least 50.

Clause 126. The composition of any one of clauses 78-125, wherein the free radical polymerization is a photopolymerization using a bisacylphosphine oxide initiator.

Clause 127. An ophthalmic device comprising the composition of any one of clauses 78-126.

Clause 128. The ophthalmic device of clause 127, wherein the ophthalmic device comprises an intraocular lens, contact lens, corneal inlay, corneal outlay, or corneal insert.

Clause 129. A method for making an ophthalmic device, the method comprising:
 a. providing a composition of any one of clauses 78-126; and
 b. forming an ophthalmic device.

Clause 130. The method of clause 129, further comprising the step of extracting the ophthalmic device with a solvent.

Clause 131. The method of clause 130, further comprising the step of hydrating the extracted ophthalmic device with at least one aqueous solution.

Clause 132. A method for making an ophthalmic device, the method comprising either:
 d. preparing a blank from the composition of any of clauses 78-126 and machining an ophthalmic device from the blank;
 e. molding an ophthalmic device from the composition of any of clauses 78-126; or
 f. molding an ophthalmic device from the composition of any of clauses 78-126 and machining the surface of the ophthalmic device.

Clause 133. The method of clause 132, further comprising the step of extracting the ophthalmic device with a solvent.

Clause 134. The method of clause 133, further comprising the step of hydrating the extracted ophthalmic device with at least one aqueous solution.

Clause 135. The method of any one of clauses 129-134, further comprising an irradiation step using a femtosecond two photon laser.

Clause 136. The method of any of clauses 129-135, further comprising a step of sterilizing the ophthalmic device.

We claim:

1. A composition made by free radical polymerization of a reactive monomer mixture comprising:
 a) at least one hydrophobic monomer,
 b) at least one hydroxyl-containing monomer,
 c) at least one tricyclo[5.2.1.0$^{2,6}$]decanedimethanol di(meth)acrylate; and
 d) at least one polyamide,
 wherein the reactive monomer mixture comprises the polyamide in an amount of about 0.10 to about 5.0 weight percent.

2. The composition of claim 1, wherein the at least one hydrophobic monomer is a hydrophobic (meth)acrylate monomer selected from a group consisting of an aliphatic (meth)acrylate, an aromatic (meth)acrylate, a cycloaliphatic (meth)acrylate, or combinations thereof.

3. The composition of claim 2, wherein the aliphatic (meth)acrylate is a $C_1$-$C_{18}$ alkyl (meth)acrylate selected from the group consisting of ethyl (meth)acrylate, n-butyl (meth)acrylate, iso-butyl (meth)acrylate, t-butyl (meth)acrylate, n-hexyl (meth)acrylate, 2-ethylhexyl (meth)acrylate, octyl (meth)acrylate, iso-decyl (meth)acrylate, heptadecyl (meth)acrylate, dodecyl (meth)acrylate, 2-propylheptyl (meth)acrylate, stearyl (meth)acrylate, and any combination thereof.

4. The composition of claim 2, wherein B aromatic (meth)acrylate is selected from the group consisting of 2-phenylethyl (meth)acrylate, 2-phenoxyethyl (meth)acrylate, 4-chlorophenoxyethyl (meth)acrylate, 3-phenylpropyl (meth)acrylate, 3-phenoxypropyl (meth)acrylate, 1,3-bis-(phenylthio)-2-propyl (meth)acrylate, poly(ethylene glycol) phenyl ether (meth)acrylate, and any combination thereof.

5. The composition of claim 2, wherein the cycloaliphatic (meth)acrylate comprises cyclohexyl (meth)acrylate, cyclopentyl (meth)acrylate, 2-cyclohexylethyl (meth)acrylate, 3-cyclohexylpropyl (meth)acrylate, norbornyl (meth)acrylate, isobornyl (meth)acrylate, ((1R,2S,4R)-bicyclo[2.2.1] hept-5-en-2-yl)methyl (meth)acrylate, ethylene glycol dicyclopentenyl ether (meth)acrylate, or any combination thereof.

6. The composition of claim 1, wherein the reactive monomer mixture comprises the at least one hydrophobic monomer in an amount between about 50 and 90 weight percent.

7. The composition of claim 1, wherein the at least one hydroxyl-containing monomer is a hydroxyalkyl (meth)acrylate selected from the group consisting of 2-hydroxyethyl (meth)acrylate, 2-hydroxypropyl (meth)acrylate, 3-hydroxypropyl (meth)acrylate, 4-hydroxybutyl (meth)acrylate, and combinations thereof.

8. The composition of claim 1, wherein the at least one hydroxyl-containing monomer is a hydroxysilicone monomer selected from the group consisting of 3-(3-(1,1,1,3,5,5, 5-heptamethyltrisiloxan-3-yl)propoxy)-2-hydroxypropyl methacrylate (SiMAA), mono-n-butyl terminated monomethacryloxypropyl terminated polydimethylsiloxane (mPDMS), or mono-(2-hydroxy-3-methacryloxypropyl)-propyl ether terminated mono-n-butyl terminated polydimethylsiloxane (OH-mPDMS), and combinations thereof.

9. The composition of claim 1, wherein the reactive monomer mixture comprises the at least one hydroxyl-containing monomer in an amount between about 1 and about 20 weight percent.

10. The composition of claim 1, further comprising a crosslinking agent is selected from the group consisting of a non-cycloaliphatic crosslinking agent, a cycloaliphatic crosslinking agent, and any combination thereof.

11. The composition of claim 10, wherein the non-cycloaliphatic crosslinking agent is selected from the group consisting of ethylene glycol di(meth)acrylate, diethylene glycol di(meth)acrylate, triethylene glycol di(meth)acrylate, tetraethylene glycol di(meth)acrylate, trimethylolpropane tri (meth)acrylate, glycerol tri(meth)acrylate, triallyl cyanurate, methylene bis(meth)acrylamide, poly(ethylene glycol) di(meth)acrylate, bis(2-hydropropyl (meth)acrylate) terminated polydimethylsiloxanes, or combinations thereof.

12. The composition of claim 10, wherein the cycloaliphatic crosslinking agent comprises cycloaliphatic groups having between one and four cycloaliphatic rings.

13. The composition of claim 1, wherein the reactive monomer mixture comprises the tricyclo[5.2.1.0$^{2.6}$]decanedimethanol di(meth)acrylate in an amount between about 1 and about 20 weight percent.

14. The composition of claim 10, wherein the non-cycloaliphatic least-ene-crosslinking agent has the formula:

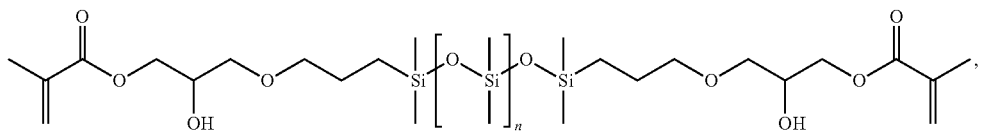

wherein n is an integer from 5 to 50.

15. The composition of claim 1, wherein the at least one polyamide is selected from poly(vinyl pyrrolidone), poly(N-vinyl-N-methyl acetamide), poly(N-vinyl acetamide), poly (dimethyl acrylamide), and a copolymer or a mixture thereof.

16. The composition of claim 1, wherein the reactive monomer mixture comprises the at least one polyamide in an amount between about 0.1 weight percent and about 3 weight percent.

17. The composition of claim 1, further comprising at least one UV absorbing compound in the reactive monomer mixture.

18. The composition of claim 1, having a water content of between about 0 weight percent and about 15 weight percent.

19. The composition of claim 1, wherein the composition has a refractive index of at least 1.45 and an Abbe number of at least 45.

20. The composition of claim 1, wherein the free radical polymerization is a photopolymerization using a bisacylphosphine oxide initiator.

21. An ophthalmic device comprising the composition of claim 1.

* * * * *